(12) United States Patent
Thomson et al.

(10) Patent No.: US 11,318,240 B2
(45) Date of Patent: May 3, 2022

(54) APPARATUS AND METHOD FOR LOCATING FLUID LEAKS IN A REDUCED PRESSURE DRESSING UTILIZING A REMOTE DEVICE

(71) Applicant: KCI Licensing, Inc., San Antonio, TX (US)

(72) Inventors: Malcolm G. Thomson, San Antonio, TX (US); Timothy Mark Robinson, Shillingstone (GB); Richard Marvin Kazala, Jr., San Antonio, TX (US); Christopher Brian Locke, Bournemouth (GB); Michael Bernard Beasley, Wimborne (GB); Larry Tab Randolph, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 347 days.

(21) Appl. No.: 15/740,768

(22) PCT Filed: Jun. 30, 2016

(86) PCT No.: PCT/US2016/040500
§ 371 (c)(1),
(2) Date: Dec. 29, 2017

(87) PCT Pub. No.: WO2017/004423
PCT Pub. Date: Jan. 5, 2017

(65) Prior Publication Data
US 2018/0318475 A1 Nov. 8, 2018

Related U.S. Application Data
(60) Provisional application No. 62/186,835, filed on Jun. 30, 2015.

(51) Int. Cl.
*A61M 1/00* (2006.01)

(52) U.S. Cl.
CPC ................ *A61M 1/73* (2021.05); *A61M 1/74* (2021.05); *A61M 1/90* (2021.05);
(Continued)

(58) Field of Classification Search
CPC .............. A61M 1/0025; A61M 1/0031; A61M 1/0088; A61M 2205/15;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Luis C. Argenta, Md and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Jessica R Arble

(57) ABSTRACT

A system and method for performing tissue therapy may include applying a reduced pressure to a tissue site of a patient. A fluid parameter associated with applying a reduced pressure to the tissue site may be sensed. An audible fluid leak location sound may be generated in response to sensing the fluid parameter. The audible fluid leak location sound may be altered in response to sensing that the fluid parameter changes. By altering the audible fluid leak loca- (Continued)

tion sound in response to sensing a change of the fluid parameter, a clinician may detect location of a fluid leak at the drape by applying force to the drape. The force applied to the drape may be a clinician pressing a finger onto an edge of the drape.

28 Claims, 13 Drawing Sheets

(52) U.S. Cl.
CPC ..... *A61M 2205/15* (2013.01); *A61M 2205/18* (2013.01); *A61M 2205/3334* (2013.01); *A61M 2205/3344* (2013.01); *A61M 2205/3576* (2013.01); *A61M 2205/505* (2013.01); *A61M 2205/6081* (2013.01)

(58) Field of Classification Search
CPC .. A61M 2205/3334; A61M 2205/3344; A61M 2205/3576; A61M 2205/505; A61M 2205/6081
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0160791 A1* | 7/2005 | Kung ................ G01N 21/05 73/24.02 |
| 2007/0060802 A1* | 3/2007 | Ghevondian ........ A61B 5/0002 600/301 |
| 2008/0071214 A1 | 3/2008 | Locke et al. |
| 2012/0035560 A1* | 2/2012 | Eddy ................ A61F 13/0203 604/313 |
| 2012/0259284 A1* | 10/2012 | Bouton .............. A61M 1/3656 604/151 |
| 2013/0228171 A1* | 9/2013 | Mansfield ........... A61M 16/044 128/202.22 |
| 2014/0116426 A1* | 5/2014 | Mullinger ............ A61M 11/005 128/200.14 |
| 2014/0309600 A1* | 10/2014 | Aceto .................. A61M 1/90 604/319 |
| 2016/0184496 A1* | 6/2016 | Jaecklein ................ A61M 1/78 604/318 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |

(56) References Cited

FOREIGN PATENT DOCUMENTS

| | | |
|---|---|---|
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2013066775 A1 | 5/2013 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, Md et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, Md., et al.; "Stimulation of Adenylate Cyclase Activity in Cultured Endothelial Cells Subjected to Cyclic Stretch"; Journal of Cardiovascular Surgery, 31,1990, pp. 634 639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 pages. English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peska, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and cerlilied translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96,167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U S S R. 1988) ("Solovev Abstract").
V.A.C.® Therapy Clinical Guidelines: A Reference Source for Clinicians; Jul. 2007.
International Search Report and Written Opinion for corresponding Application No. PCT/US2016/040500, dated Oct. 6, 2016.

* cited by examiner

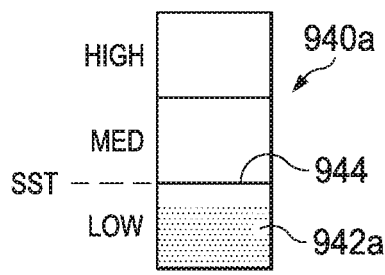
FIG. 11A
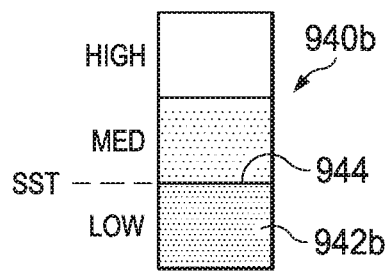
FIG. 11B
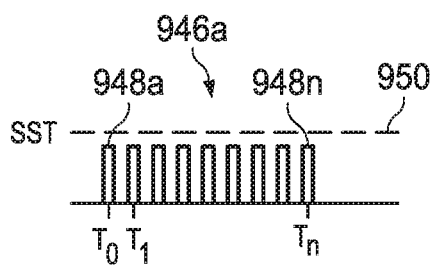
FIG. 11C
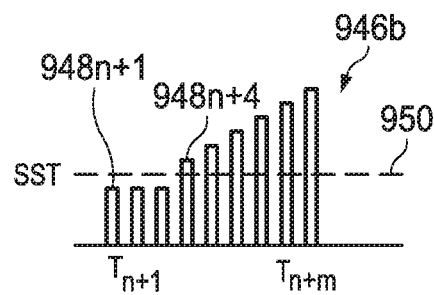
FIG. 11D
Leakage Rate: _1_ ← 952a
FIG. 11E
Leakage Rate: _5_ ← 952b
FIG. 11F
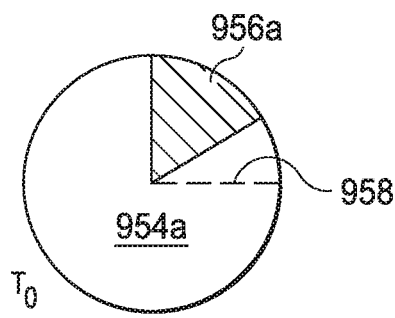
FIG. 11G
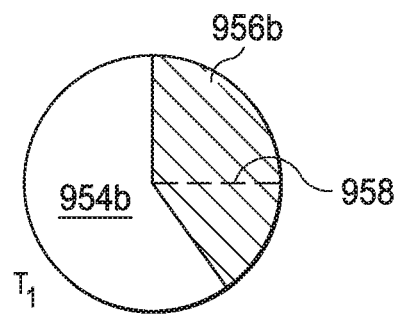
FIG. 11H

APPARATUS AND METHOD FOR LOCATING FLUID LEAKS IN A REDUCED PRESSURE DRESSING UTILIZING A REMOTE DEVICE

RELATED APPLICATIONS

This application claims the benefit, under 35 USC 119(e), of the filing of U.S. Provisional Patent Application No. 62/186,835, entitled "Apparatus and Method for Locating Fluid Leaks in a Reduced Pressure Dressing Utilizing a Remote Device," filed Jun. 30, 2015, which is incorporated herein by reference for all purposes.

TECHNICAL FIELD

This invention relates generally to an apparatus and method of promoting tissue growth, and more specifically, an apparatus and method for detecting fluid leaks of a dressing positioned at a tissue site being treated by a reduced pressure delivery system.

BACKGROUND

Tissue growth and wound healing of patients has been shown to be accelerated through the use of applying reduced pressure to a tissue site. Reduced pressure delivery systems operate to form such a reduced pressure at a tissue site of a patient. This form of wound healing can be readily integrated into a clinician's wound healing procedures. Reduced pressure tissue therapy optimizes patient care and decreases costs associated with treatment of patients having traumatic and chronic wounds. Reduced pressure therapy can be administered in hospitals, community settings, such as assisted living complexes and convalescences homes, or homes of patients.

Reduced pressure delivery to a wound or tissue site promotes wound healing and/or tissue growth, in part, by removing infectious materials and other fluids from the wound or tissue site. Reduced pressure treatment further promotes tissue growth by imposing forces on the tissue, thereby causing micro-deformation of the tissue, which is believed to contribute to the development of granulation tissue at the tissue site. The forces imposed on the tissue site by the delivery of reduced pressure further encourages improved blood flow at the tissue site, which further assists in the growth of new tissue.

Reduced pressure delivery systems generally use a vacuum pump to apply a reduced pressure via a reduced pressure conduit to a tissue site. A manifold is often used at the tissue site to help evenly distribute the reduced pressure. A drape is typically used to cover the manifold and form a seal with surrounding tissue of the tissue site to which the reduced pressure is being applied. In order to maintain the reduced pressure at a relatively constant and accurate reduced pressure to provide optimum tissue therapy, the drape is to be interfaced and maintained with the healthy tissue surrounding the tissue site, i.e., the peri-tissue, to minimize the number and severity of the fluid leaks, such as air leaks. In the event that a fluid leak results during installation of the drape or during treatment, clinicians often find it difficult to isolate the precise location of the fluid leak.

When a reduced pressure dressing is applied to a patient's body, a visual inspection is made to confirm that the constituent parts of the dressing such as, for example, the drape covering a porous pad and a connector for providing the reduced pressure to the porous pad, have been placed correctly to form a leak-free seal over the tissue site. As the therapy device begins applying reduced pressure in operation, the reduced pressure increases from ambient pressure during a start-up period until a desired target pressure is reached and maintained. The application of reduced pressure causes the reduced pressure dressing to contract in response to the increasing pressure. After the start-up period, a controller regulates the reduced pressure during a therapy period based on the therapy intended for treating the patient. Fluid leaks can occur during the start-up and/or the therapy periods as a result of the initial misplacement of these components or subsequent damage to the drape itself. Locating such fluid leaks in reduced pressure dressings can be time-consuming and difficult to correct.

Even though some drape material may be transparent so that the wound and dressing can be seen by the clinician, visual inspection through the drape material only helps to locate the largest holes or leaks in the drape or other damage to the dressing that is causing major leaks allowing air to leak into the tissue site. While the clinical benefits of reduced-pressure therapy are widely known, the complexity of reduced-pressure therapy can be a limiting factor in its application and further development of reduced-pressure systems which presents significant challenges to manufacturers, healthcare providers, and patients.

SUMMARY OF THE INVENTION

To overcome the problem of locating fluid leaks at an interface between a reduced pressure dressing and tissue of a patient, new and useful systems, apparatuses, and methods for detecting location of fluid leaks at the dressing of reduced pressure delivery systems are set forth in the appended claims. Illustrative embodiments are also provided to enable a person skilled in the art to make and use the claimed subject matter.

One embodiment of a system for performing reduced pressure tissue therapy may comprise a reduced pressure delivery system configured to apply a reduced pressure provided by a reduced pressure source to a tissue site, and a drape configured to be positioned over the tissue site to maintain the reduced pressure at the tissue site. The system may further comprise a mobile device having a microphone operable to be positioned at a first location proximate the drape to sense a sound pressure wave propagating from the drape at the first location, and configured to generate a first audio signal having amplitude and frequency components indicative of a fluid leak at the first location when a fluid leak is present in or proximate the drape.

In another embodiment of a system, the mobile device may be further configured to compare an amplitude average of the amplitude components of the first audio signal over time to an amplitude threshold indicative of a fluid leak at the first location, and to generate an output signal indicating the presence of a fluid leak at the first location if the amplitude average is greater than the amplitude threshold. The microphone may be operable to be positioned at a second location proximate the drape to sense a sound pressure wave propagating from the drape at the second location, and configured to generate a second audio signal having amplitude and frequency components indicative of a fluid leak at the second location when a fluid leak is present in or proximate the drape. The mobile device is further configured to compute a first amplitude average of the amplitude components of the first audio signal over time and a second amplitude average of the amplitude components of the second audio signal over time, and to compute an amplitude difference between the second amplitude average and the first amplitude average. The mobile device may then be configured to generate an output signal indicating the presence of a fluid leak if the amplitude difference is greater than an amplitude differential threshold indicative of a fluid leak at the second location.

In another embodiment of the system, the mobile device may be configured to filter frequency components of the first audio signal to pass filtered frequencies corresponding to the sound pressure waves at locations proximate the drape, to compare a frequency average of the filtered frequencies of the first audio signal to a frequency threshold indicative of a fluid leak at the first location, and to generate an output signal indicating the presence of a fluid leak at the first location if the frequency average is greater than the frequency threshold. The microphone may be operable to be positioned at a second location proximate the drape to sense a sound pressure wave propagating from the drape at the second location, and configured to generate a second audio signal having amplitude and frequency components indicative of a fluid leak at the second location when a fluid leak is present in or proximate the drape. The mobile device may be further configured to filter frequency components of the first audio signal and the second audio signal to pass filtered frequencies corresponding to the sound pressure waves at locations proximate the drape, and further configured to compute a first frequency average of the filtered frequencies of the first audio signal and a second frequency average of the filtered frequencies of the second audio signal. The mobile device may be configured further to compute a frequency differential between the second frequency average and the first frequency average, and further configured to generate an output signal indicating the presence of a fluid leak if the frequency differential is greater than a frequency differential threshold indicative of a fluid leak at the second location.

One embodiment of a method for performing reduced pressure tissue therapy may comprise applying a reduced pressure to a tissue site of a patient covered by a drape, sensing a sound pressure wave propagating from the drape at a first location proximate the drape, and generating a first audio signal representing the sound pressure wave. The method may further comprise computing an amplitude average of the amplitudes of the first audio signal over time, comparing the amplitude average of the first audio signal to an amplitude threshold indicative of a fluid leak at the first location, and then generating an output signal indicating the presence of a fluid leak at the first location if the amplitude average is greater than the amplitude threshold.

Another embodiment of a method for performing reduced pressure tissue therapy may comprise applying a reduced pressure to a tissue site of a patient covered by a drape, sensing a sound pressure wave propagating from the drape at a first location proximate the drape, and generating a first audio signal representing the sound pressure wave. The method may further comprise filtering the frequencies of the first audio signal to pass filtered frequencies corresponding to the sound pressure waves at locations proximate the drape, and computing a frequency average of the filtered frequencies of the first audio signal. The method may comprise further comparing the frequency average of the first audio signal to a frequency threshold indicative of a fluid leak at the first location, and then generating an output signal indicating the presence of a fluid leak at the first location if the frequency average is greater than the frequency threshold.

Yet another embodiment of a method for performing reduced pressure therapy may comprise applying a reduced pressure to a tissue site of a patient covered by a drape, sensing sound pressure waves propagating from the drape at a first location proximate the drape and a second location proximate the drape, and generating a first audio signal and a second audio signal representing the sound pressure waves. The method may comprise further computing a first amplitude average of the amplitudes of the first audio signal over time and a second amplitude average of the amplitudes of the second audio signal over time, and then computing an amplitude difference between the second amplitude average in the first amplitude average. The method may comprise further comparing the amplitude average of the first audio signal to an amplitude threshold indicative of a fluid leak at the first location, and generating an output signal indicating the presence of a fluid leak if the amplitude difference is greater than an amplitude differential threshold indicative of a leak at the second location.

And yet another embodiment of a method for performing reduced pressure therapy may comprise applying a reduced pressure to a tissue site of a patient covered by a drape, sensing sound pressure waves propagating from the drape at a first location proximate the drape and a second location proximate the drape, and generating a first audio signal representing the sound pressure waves and a second audio signal representing the sound pressure waves. The method may comprise further filtering the frequencies of the first audio signal and the second audio signal to pass filtered frequencies corresponding to the sound pressure waves at locations proximate the drape, and computing a first frequency average of the filtered frequencies of the first audio signals and a second frequency average of the filtered frequencies of the second audio signal. The method may comprise further computing a frequency differential between the second frequency average and the first frequency average; and generating an output signal indicating the presence of a fluid leak if the frequency differential is greater than a frequency differential threshold indicative of a fluid leak at the second location.

One additional embodiment of an apparatus for detecting fluid leaks in a reduced pressure therapy system may comprise a housing sized and adapted to be in the form of a hand-held tool, a microphone positioned within the housing, a computing device electrically coupled to the microphone, a display disposed on a surface of the housing, and a communications interface. The microphone may be operable to sense a sound pressure wave propagating from a drape positioned over a tissue site, and configured to generate a first audio signal and the computing device may be configured to receive and process the first audio signal to determine an existence of a fluid leak at the drape. The display may be configured to provide output indicative of the existence of a fluid leak, and the communications interface may be configured to transmit and receive data related to the existence of a fluid leak with a reduced pressure therapy system.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

A more complete understanding of the apparatuses and methods of the claimed inventions may be obtained by reference to the following Detailed Description when taken in conjunction with the accompanying Drawings wherein:

FIGS. 11A-11H are depictions of exemplary indicators for display on the graphical user interface of FIG. 11 to enable a clinician to view while locating a fluid leak at a drape;

DESCRIPTION OF THE EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
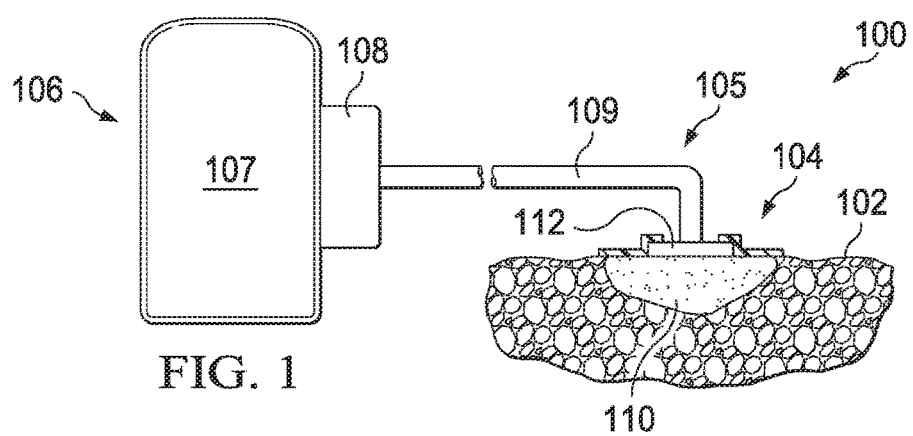
FIG. 1 is an illustration of an exemplary configuration of a patient being treated using a reduced pressure delivery system.

With regard to FIG. 1, apparatus 100 for treating a patient 102 by providing reduced pressure therapy to a tissue site 104 of the patient 102 is shown. The apparatus 100 comprises certain reduced pressure dressing components (dressing components 105) and a reduced pressure therapy system 106 that is fluidly coupled to the tissue site 104 via the dressing components 105 to provide reduced pressure treatment to the patient 102. The reduced pressure therapy system 106 may include a reduced pressure delivery system 107 (delivery system 107) and a canister or container 108 for collecting bodily fluids from the tissue site 104. The dressing components 105 include a reduced pressure conduit 109 fluidly coupled between the delivery system 106 to the tissue site 104, and may also be coupled to the fluid container 108 for collecting bodily fluids from the tissue site 104. Reduced pressure from the conduit 109 may be distributed to the tissue site 104 via a reduced pressure dressing or manifold (not shown) located at or within the tissue site 104. The dressing components 105 may also include a drape 110 that may be placed over the tissue site 104 and distribution manifold to seal the distribution manifold at the tissue site 104. The drape 110 may be constructed from a flexible material that is impermeable to fluids including gases and liquids to prevent air or other fluids from entering or exiting the tissue site 104 during reduced pressure treatment. The dressing components 105 may also include a connector 112 that fluidly couples the conduit 109 to the reduced pressure dressing or manifold through the drape 110.

As used herein, the term "flexible" refers to an object or material that is able to be bent or flexed. Elastomer materials are typically flexible, but reference to flexible materials herein does not necessarily limit material selection to only elastomers. The use of the term "flexible" in connection with a material or reduced pressure delivery apparatus in accordance with the principles of the present invention generally refers to the material's ability to conform to or closely match the shape of a tissue site. For example, the flexible nature of a reduced pressure delivery apparatus used to treat a bone defect may allow the apparatus to be wrapped or folded around the portion of the bone having the defect.

The term "fluid" as used herein generally refers to a gas or liquid, but may also include any other flowable material, including but not limited to gels, colloids, and foams. One example of a fluid is air.

The term "impermeable" as used herein generally refers to the ability of a membrane, cover, sheet, or other substance to block or slow the transmission of either liquids or gas. Impermeable may be used to refer to covers, sheets, or other membranes that are resistant to the transmission of liquids, while allowing gases to transmit through the membrane. While an impermeable membrane may be liquid type, the membrane may simply reduce the transmission rate of all or only certain liquids. The use of the term "impermeable" is not meant to imply that an impermeable membrane is above or below any particular industry standard measurement for impermeability, such as a particular value of water vapor transfer rate (WVTR).

The term "manifold" as used herein generally refers to a substance or structure that is provided to assist in applying reduced pressure to, delivering fluids to, or removing fluids from a tissue site. A manifold typically includes a plurality of flow channels or pathways that interconnect to improve distribution of fluids provided to and removed from the area of tissue around the manifold. Examples of manifolds may include, without limitation, devices that have structural elements arranged to form slow channels, cellular foams, such as open-desk cell foam, porous tissue collections, and liquids, gels and foams that include or cure to include flow channels.

The term "reduced pressure" as used herein generally refers to a pressure less than the ambient pressure at a tissue site that is being subjected to treatment. In most cases, this reduced pressure will be less than the atmosphere pressure at which the patient is located. Alternatively, the reduced pressure may be less than a hydrostatic pressure of tissue at the tissue site. Although the terms "vacuum" and "negative pressure" may be used to describe the pressure applied to the tissue site, the actual pressure applied to the tissue site may be significantly less than the pressure normally associated with a complete vacuum. Reduced pressure may initially generate fluid flow in the tube or conduit in the area of the tissue site. As the hydrostatic pressure around the tissue site approaches the desired reduced pressure, the flow may subside, and the reduced pressure is then maintained. Unless otherwise indicated, values of pressures stated herein are gage pressures.

The term "scaffold" as used herein refers to a substance or structure used to enhance or promote the growth of cells and/or the formation of tissue. A scaffold is typically a three dimensional porous structure that provides a template for cell growth. The scaffold may be infused with, coated with, or comprised of cells, growth factors, or other nutrients to promote cell growth. A scaffold may be used as a manifold in accordance with the embodiments described herein to administer reduced pressure tissue treatment to a tissue site, as well as providing a template for cell growth.

The term "tissue site" as used herein refers to a wound or defect located on or within any tissue, including but not limited to, bone tissue, adipose tissue, muscle tissue, neuro tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The term "clinician" is used herein as meaning any medical professional, user, family member of a patient, or patient who interacts or interfaces with a delivery system.

Figure 2:
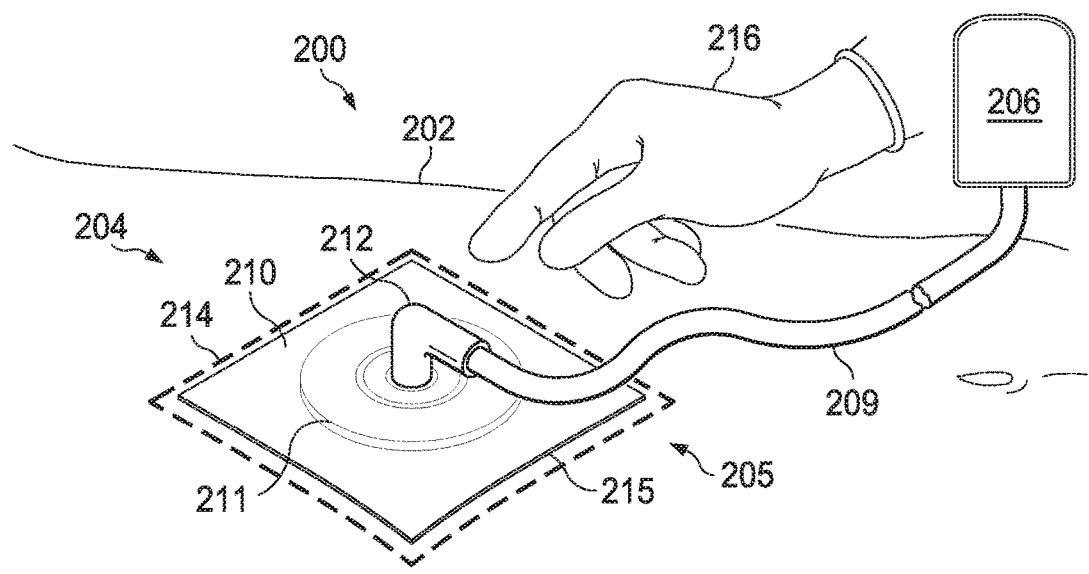
FIG. 2 is an illustration of an exemplary drape covering a tissue site to which reduced pressure is being applied by a reduced pressure delivery system.

Referring to FIG. 2, apparatus 200 for treating a patient 202 by providing reduced pressure therapy to a tissue site 204 of the patient 202 is shown. The apparatus 200 comprises certain reduced pressure dressing components (dressing components 205) and a reduced pressure therapy system 206, which are substantially similar to the apparatus 100 described above in FIG. 1 as indicated by similar reference numbers. The reduced pressure therapy system 206 is fluidly coupled to the tissue site 204 via the dressing components 205 to provide reduced pressure treatment to the patient 202. The reduced pressure therapy system 206 may include the reduced pressure delivery system 107 (delivery system 107) and the canister or container 108 for collecting bodily fluids from the tissue site 204. The dressing components 205 of the apparatus 200 may include a reduced pressure conduit 209 fluidly coupled between the delivery system 206 to the tissue site 204, and may also be coupled to the fluid container 108 for collecting bodily fluids from the tissue site 204. Reduced pressure from the conduit 209 may be distributed to the tissue site 204 via a reduced pressure dressing or manifold (not shown) located at or within the tissue site 204. The dressing components 205 may also include a drape 210 that may be placed over the tissue site 204 and distribution manifold to seal the distribution manifold at the tissue site 204. The drape 210 may be constructed from a flexible material that is impermeable to liquids and/or gases to prevent air or other fluids from entering or exiting the tissue site 204 during reduced pressure treatment. The dressing components 205 may also include a connector 212 that fluidly couples the conduit 209 to the reduced pressure dressing or manifold through the drape 210.

The drape 210 may be configured to form a visible outline 211 of the manifold when the drape 210 covers the distribution manifold as a result of the distribution manifold being pressed into the drape 210 to form the outline 211. The drape 210 covers the tissue site 204, thereby helping to maintain a seal at the tissue site 204 so that fluids, such as air, cannot enter or exit the tissue site. Preventing fluids from entering or exiting the tissue site 204 minimizes fluid leakage so that (i) a desired amount of reduced pressure therapy is provided to the tissue site 204, (ii) the reduced pressure is delivered at a desired rate, and (iii) the reduced pressure is maintained at a desired target pressure for any desired amount of time. Minimizing fluid leakage into the tissue site under the drape 210 also minimizes the chance of infection from the air and other contaminants surrounding the tissue site and facilitates growth of new tissue.

The process for dressing a wound at a tissue site comprises positioning the distribution manifold adjacent the tissue site 204. As part of the process, a clinician may cover both the distribution manifold and the tissue site with the drape 210 and apply a force to the drape 210 prior to and during operation of the delivery system. By applying a force along the outer edges 215 of the drape 210, the clinician may create or otherwise improve the seal formed between the drape 210 and peri-tissue 214 surrounding the tissue site 204 at an intersection (not shown) between the drape 210 and the peri-tissue 214. If the seal is not completely formed or a fluid leak subsequently develops, the clinician may press a finger 216 along the outer edges 215 of the drape 210 to improve or re-establish the seal at the intersection between the drape 210 in the peri-tissue 214. Locating a fluid leak in the drape 210, e.g., a small hole or tear in the drape 210, or a fluid path between the drape 210 and the peri-tissue 214 is often difficult in practice as described above.

Figure 3:
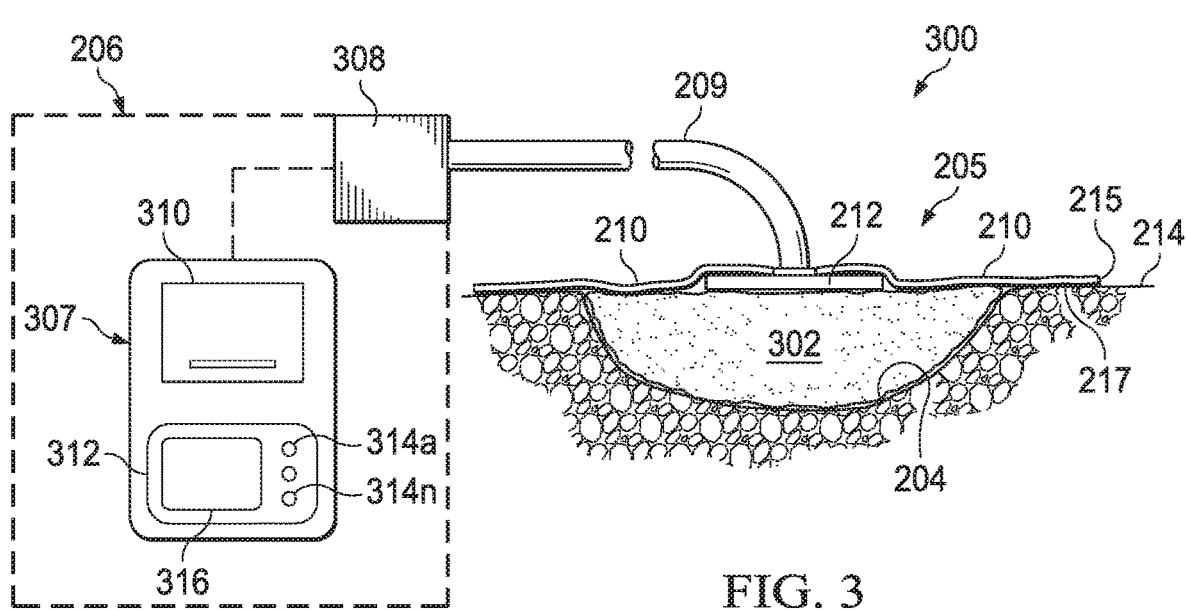
FIG. 3 is an illustration of an exemplary drape covering a tissue site to which reduced pressure is being applied by a reduced pressure delivery system.

Referring to FIG. 3, apparatus 300 for treating a patient by providing reduced pressure therapy to the tissue site 204 of the patient is shown and comprises the dressing components 205 shown in cross-section and a reduced pressure therapy system 206 of FIG. 2. The drape 210 extends over a distribution manifold 302 and the tissue site 204 to provide a seal so that the distribution manifold 302 is in fluid communication with reduced pressure conduit 209 as described above. The seal is formed between the drape 210 and peri-tissue 214 surrounding the tissue site 204 at an intersection 217 between the drape 210 and the peri-tissue 214. The drape 210 may be placed over or under the connector 212 and may be an integral component with a connector 212. The drape 210 may also adhere to the connector 212 with an adhesive, or welded or otherwise sealed to the connector 212.

The reduced pressure conduit 209 is also in fluid communication with a canister 308 and a delivery system 307 of the reduced pressure therapy system 206, both of which may be similar to the canister 108 and the delivery system 107 shown in FIG. 1. The delivery system 307 may include a vacuum pump 310 and electronic display 312. The electronic display 312 may include control elements 314a-314n (collectively 314) that may be used by a user or clinician operating the reduced pressure therapy system 206. In addition or alternatively, the electronic display 312 may include a touch-screen 316 that enables the user or clinician to interface with and operate the reduced pressure therapy system 206.

If a fluid leak develops at the intersection 217 between the drape 210 in the peri-tissue 214 or anywhere in the drape 210, then a fluid leak sensor (not shown) may generate and communicate a fluid leak signal that may be provided to the delivery system 307. The fluid leak signal may represent or be analogous to a fluid parameter indicative of or responsive to an event wherein the fluid leak exceeds a predetermined airflow level or threshold. A processing unit (not shown) that may be a component of the delivery system 307 may respond by generating a fluid leak alarm in an audible and/or visual manner. For example, a buzzer, bell, recorded message, or other audible sound may be generated to alert a clinician that a fluid leak has occurred at the intersection 217 between the drape 210 and the peri-tissue 214. To locate the fluid leak at the drape 210, the clinician may engage a fluid leak mode that may be automatically or manually entered at the delivery system 307. The fluid leak mode may be used to enable the clinician to apply a force, such as pressing a finger around the outer edges 215 of the drape 210 or pressing the drape 210 around the intersection 217. As the clinician applies force to the drape 210 at either point, the delivery system 307 may generate an audible sound that changes in response to a change in the leak rate as a result of pressure being applied to the specific location where the fluid leak exists. The audible sound may be decreased in pitch or volume, for example, to enable the clinician to identify the location on the drape 210 so that the fluid leak may be corrected.

Figure 4:
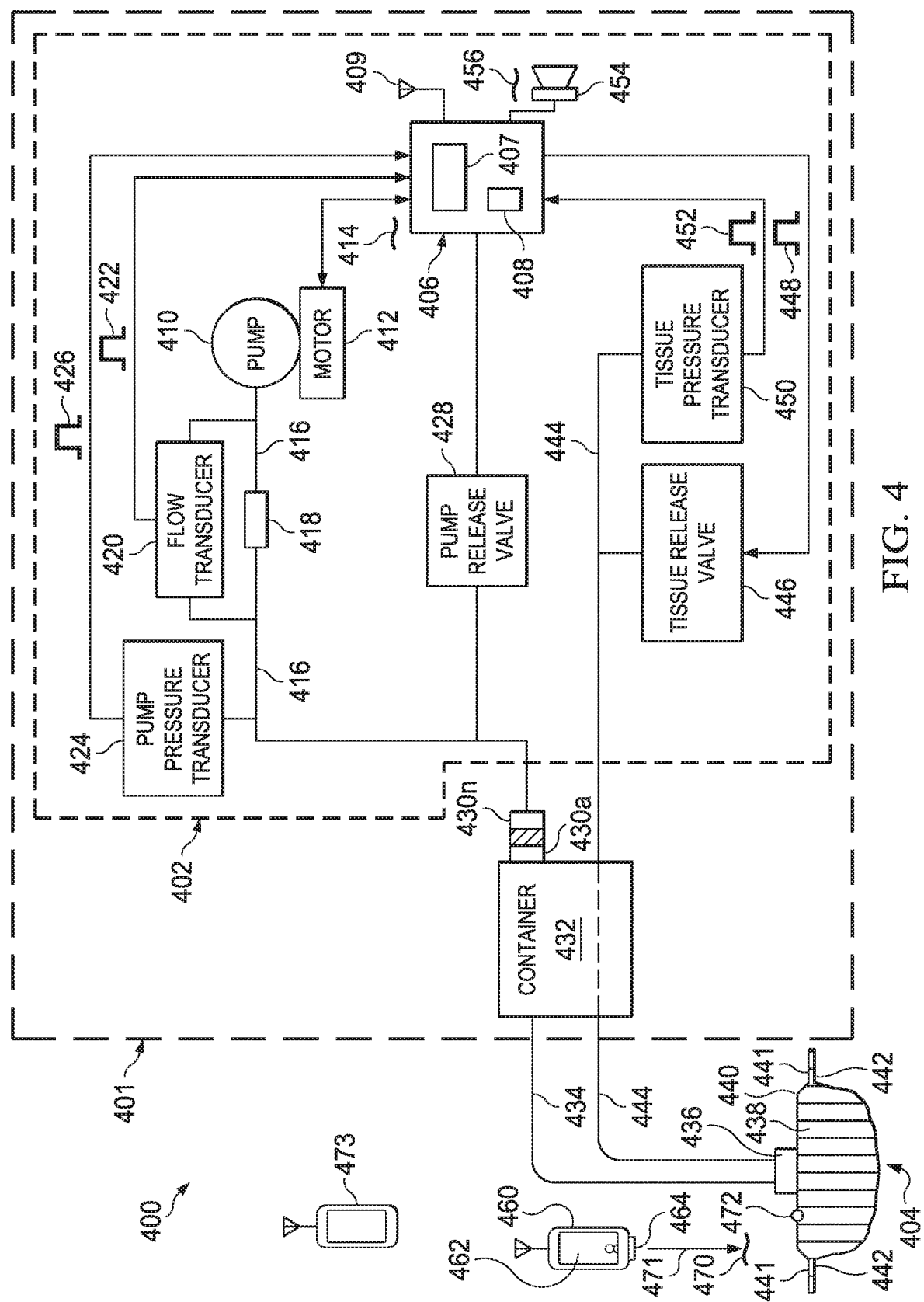
FIG. 4 is a block diagram of an exemplary reduced pressure delivery system configured to apply reduced pressure to a tissue site and a mobile device configured to sense sound pressure waves indicative of fluid leaks associated with a drape such as, for example, the drape of FIG. 3.

Referring now to FIG. 4, apparatus 400 for treating a patient by providing reduced pressure therapy to a tissue site of the patient includes a reduced pressure therapy system 401. The reduced pressure therapy system 401 comprises a delivery system 402 that is shown as applying reduced pressure to tissue site 404. The delivery system 402 may include a controller 406 that includes a processing unit 408. The controller 406 may also include an electronic display device 407 and a receiver transmitter module (not shown) including an antenna 409 for receiving and transmitting signals for displaying information related to fluid parameters and communicating with other devices such as, for example, mobile devices. The processing unit 408 may include one or more processors, logic, analog components, or any other electronics that enable signals including information, such as fluid pressure at a tissue site 404 or airflow out of the tissue site 404, to be received by the receiver. The processing unit 408 may process the information provided by such signals. For example, a fluid leak signal may be received by the processing unit 408 and a fluid leak alarm and/or fluid leak location process may be computed and provided by the processing unit 408.

The delivery system 402 may further include a pump 410, such as a vacuum pump, that may be driven by a motor 412. The motor 412 may be in electrical communication with the controller 406 and respond to control signals 414 generated by the controller 406 to adjust the desired speed of the pump 410 to generate and maintain the desired pressure. The motor 412 may also provide information to the controller 406 indicative of the pressure being applied to the tissue site 404. The pump 410 is fluidly connected to a reduced pressure conduit 416. The reduced pressure conduit 416 may include an orifice 418 that operates as a relief valve. In parallel with the orifice is a flow transducer 420 that may be configured to determine flow rate of fluid passing through the reduced pressure conduit 416. The flow transducer 420 is fluidly connected to the reduced pressure conduit 416 and configured to generate a flow rate signal 422 including information indicative of flow rate of a fluid within the reduced pressure conduit 416.

A pump pressure transducer 424 may be connected to reduced pressure conduit 416 to convert pressure in the reduced pressure conduit 416 and communicate a pump pressure signal 426 including information indicative of fluid pressure in the reduced pressure conduit 416 to the controller 406. The pump pressure signal 426 may be digital or analog. A pump release valve 428 may also be connected to the reduced pressure conduit 416 and be configured to release pressure from the reduced pressure conduit 416 in case of an emergency situation or otherwise.

The reduced pressure therapy system 401 may further include one or more filters 430a-430n (collectively 430) and a container 432 that are in fluid communication with the reduced pressure conduit 416. The filters 430 may be in fluid communication with the container 432, which is used to collect fluids from tissue site 404. The filters 430 may be configured to prevent fluids collected in the container 432 from entering the reduced pressure conduit 416. The container 432 may further be in fluid communication with reduced pressure conduit 434. Although shown as separate conduits, the reduced pressure conduits 416 and 434 may be the same or different material and have the same or different dimensions. The reduced pressure conduit 434 may connect to or be in fluid communication with a connector 436, which may be connected to a distribution manifold 438 to distribute reduced pressure across the tissue site 404. Drape 440 extends over the tissue site 404 on peri-tissue 442 surrounding the tissue site 404 to form a seal at an intersection 441 to generate and maintain reduced pressure at the tissue site 404 as described above.

A feedback reduced pressure conduit 444 may pass through container 432. A tissue release valve 446 may be connected to the feedback reduced pressure conduit 444 to enable pressure to be released at the tissue site 404 in response to a command signal 448 generated by the processing unit 408. The command signal 448 may be generated by the processing unit 408 in response to the processing unit 408 receiving a sensor signal, such as flow rate signal 422 crossing a threshold level as described above. Alternatively, the command signal 448 may be generated in response to a clinician selectively stopping the delivery system 402 via a user interface (not shown). Other events, such as the completion of a treatment cycle may cause the processing unit to generate the command signal 448 to activate the tissue release valve 446. In another example, a tissue pressure transducer 450 may be used to convert pressure sensed at the tissue site 404 and provide a feedback signal 452 to the processing unit 408. In response to the processing unit 408 determining that pressure sensed at the tissue site 404 sensed is above a threshold value, the processing unit 408 may communicate command signal 448 to the tissue release valve 446 for release of tissue pressure.

A speaker 454 may be in electrical communication with the controller 406 to generate an audible sound as an alert along with the information being provided to the clinician on the electronic display device 407. In the event that the processing unit 408 determines that a fluid parameter, such as pressure at the tissue site 404 or flow rate of fluid through the reduced pressure conduit 416 crosses a threshold value, the controller 406 may generate an audio signal 456 that may be communicated to the electronic speaker 454 for providing an audible sound. For example, the processing unit 408 may determine that a fluid leak exists at the tissue site 404 because the fluid flow rate increases above a predetermined flow rate threshold level. In response to determining that the flow rate level sensed by the flow transducer 420 has been exceeded, the processing unit 408 may generate the audio signal 456 and communicate an alert signal to the electronic speaker 454 to notify a clinician that a problem exists. In another example, a sensor such as tissue pressure transducer 450 may sense a fluid parameter at the tissue site 404 and the processing unit 408 may determine that the pressure at the tissue site 404 has decreased below a desired level. Still yet, rather than directly sensing a fluid parameter, an indirect measurement may be performed by measuring power or voltage being applied to the motor 412 that may vary based on the load on the pump 410 to determine approximate fluid flow. The voltage may be a pulse width modulated voltage that varies based on the duty cycle so that the duty cycle may be measured to determine the approximate fluid flow. The processing unit 408 may also communicate with a mobile device that directly senses a fluid parameter and transmits such information back to the controller 406 to alert the clinician of a problem.

The processing unit 408 may be selectively programmed or commanded to begin a fluid leak mode for enabling the clinician to determine whether a fluid leak has developed at the drape 440 by applying a force on the edges of the drape 440 or around the upper surface of the drape 440 above the peri-tissue 442. The processing unit 408 may generate a continuous or discontinuous fluid leak signal and drive the electronic speaker 454 to enable the clinician to determine a location of the fluid leak at the drape 440. Although the fluid leak mode is helpful for locating a fluid leak at the drape 440, it should be understood that the fluid leak mode may not enable the clinician to precisely locate the specific location of fluid leaks proximate the drape 440. When referring to fluid leaks proximate the drape 440, such leaks may include, for example, fluid leaks extending through the drape 440 to the distribution manifold 438, fluid passageways at the intersection 441 between the drape 440 and the peri-tissue 442, or fluid leaks between the drape 440 and the connector 436. The fluid leak mode may also help a clinician locate a fluid leak at a conduit connection or other location in the system. In one embodiment, a connector (not shown) may be provided to cause the reduced pressure conduits 416 and 434 to simulate operation with a drape seal that is satisfactory (e.g., an acceptable level of fluid leakage) to enable the clinician to locate fluid leaks at or within the reduced pressure delivery system.

The apparatus 400 and/or the reduced pressure therapy system 401 may further comprise a computing device and a microphone electrically and operatively coupled to the computing device. The computing device may be selectively programmed to provide a leak location mode (as distinguished from the fluid leak mode described above) for enabling the clinician to identify the location of a fluid leak proximate to the drape 440 by sensing sound waves or audio waves generated by such leak and then providing a leak location signal in response to the sound waves, without the clinician having to go through the meticulous process of applying force to the drape 440 as described above. The computing device also may be electrically coupled to the processing unit 408 by either wire or wireless means such as, for example, a Wi-Fi or Bluetooth® connection. The microphone may be any type of an acoustic-to-electric transducer or sensor that converts sound into an electrical signal and can be electrically coupled to the computing device by wire or wireless means such as, for example, a Wi-Fi or Bluetooth® connection. More specifically, the microphone may sense sound waves or audio waves generated by a fluid leak and then provide a leak location signal in response to the sound waves, which may indicate the existence and/or location of the fluid leak.

The microphone is sufficiently small and mobile to allow clinicians to more easily and conveniently (i) indicate whether a fluid leak exists by providing a signal to the clinician such as, for example, an alarm, and (ii) identify the specific location of such fluid leak as the clinician moves the microphone along the surface of the drape 440 tracing an outline of the drape 440 from one location to another location on the drape 440. The leak location mode may also use the microphone and computing device to sense any background or ambient noise proximate the drape 440 which may be filtered out to more accurately identify the occurrence and location of a fluid leak. The leak location mode may also comprise means for determining (i) a warm-up period during which the reduced pressure pump 410 initially increases the reduced pressure to a predetermined target pressure and (ii) operational periods during which the reduced pressure pump 410 is engaged to maintain the reduced pressure at the tissue site proximate the target pressure.

The computing device may be, for example, a mobile device which may be electrically and operatively coupled to the microphone as described above or may include an integrated microphone for sensing sounds generated by a fluid leak proximate the drape 440 and providing a leak location signal in response to the sound as described above. The computer device or mobile device may be programmed to implement the software algorithms shown in FIGS. 8, 9, 12A and 12B and described in the corresponding portions of the specification for processing the leak location signal provided by the microphone for identifying and locating fluid leaks. The mobile device may be packaged or constructed as a single unit that integrates the computer device and the microphone in a single device such as, for example, a smart phone, tablet, or other device that is capable of storing software applications, e.g., leak detection application, programmed for a specific operating system (e.g., iOS, Android, and Windows) that is used to read in and interpret sound received by the microphone of the mobile device to indicate changes in the relative sound pressure. The computing device may also comprise a more stationary computer such as, for example, a desktop computer operatively coupled to the microphone that can be positioned proximate the surface of the drape 440 for sensing sounds generated by a fluid leak proximate the drape 440 as described above.

As indicated above, the mobile device may be a single unit such as, for example, mobile device 460 that includes an integrated microphone 464 used to sense sound pressure such as, for example, sound wave 470 as indicated by arrow 471. The sound wave 470 may be generated by a fluid leak such as, for example, a small hole 472 in the drape 440 among other types of fluid leaks as described above. The microphone 464 of the mobile device 460 senses the sound waves 470 when disposed proximate the drape 440 to facilitate the presence and location of such fluid leaks. The mobile device 460 may also include an electronic display device 462 to provide visual images to a clinician or patient including, for example, graphical user interfaces (GUIs), haptics, and/or speakers as described above that provide information relating to various alarms that a fluid leak is present and changes in relative sound pressure waves that are indicative of the size and/or location of the fluid leak sensed by the microphone 464 and processed by the mobile device 460.

A clinician may use the microphone 464 of the mobile device 460 to detect sound pressure waves 470 generated by one of such fluid leaks to more easily and immediately identify the location of such fluid leak in-situ that may be corrected to more quickly generate or maintain reduced pressure at the tissue site 404. The mobile device 460 may also provide such information to the controller 406 to alert a clinician who may be monitoring the delivery system 402 several feet away from the tissue site 404. The mobile device 460 may also provide such information to another mobile device such as, for example mobile device 473 to remotely monitor such information. The leak detection application on the mobile device 460 may also be used to receive instructions from a clinician using either the delivery system 402 or the other mobile device 473. For example, the clinician may have received an audible alarm from the speaker 454 of controller 406 and may inform the patient that a serious fluid leak has occurred somewhere in the dressing as described above and below in more detail. The clinician might then instruct the patient to use the mobile device 460 to specifically locate the fluid leak and determine the size of the fluid leak or the airflow escaping from the fluid leak.

When the clinician uses the microphone 464 of the mobile device 460 to detect sound pressure waves 470 generated by a fluid leak, the audio signal received by the microphone 464 may be sampled and analyzed to detect the presence and/or severity of a fluid leak utilizing a leak detection application that is loaded on a mobile device such as, for example, the mobile device 460. The audio signal received by the microphone 464 may be sampled by the leak detection application at a regular interval, i.e., the sample rate, and then quantized to discrete values within a fixed range such as, for example, a fixed range governed by a bit depth of 16-bits (i.e. pulse code modulation). The sample values may be, for example, integers between −32768 and +32767 and the frequency of the sample rate may be between 8 kHz and 44.1 kHz. To search for fluid leaks, the clinician monitors the electronic display 462 of the mobile device 460 and/or listens to the audio output signal while slowly moving the mobile device 460 over the surface of the drape 440 until a graphical or audible indicator signals the location of a potential leak.

Figure 5A:
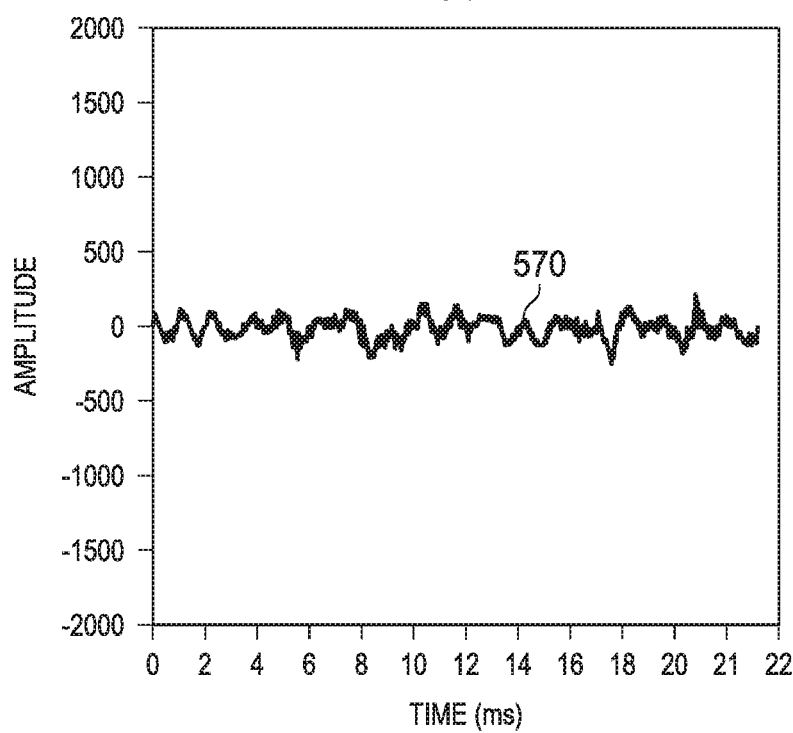
FIGS. 5A and 5B are graphs of amplitudes of audio signals sensed by a microphone of the mobile device of FIG. 4 to indicate the detection of fluid leaks associated with the drape, wherein FIG. 5A indicates that no leak is present and FIG. 5B indicates the presence of a fluid leak.
Figure 5B:
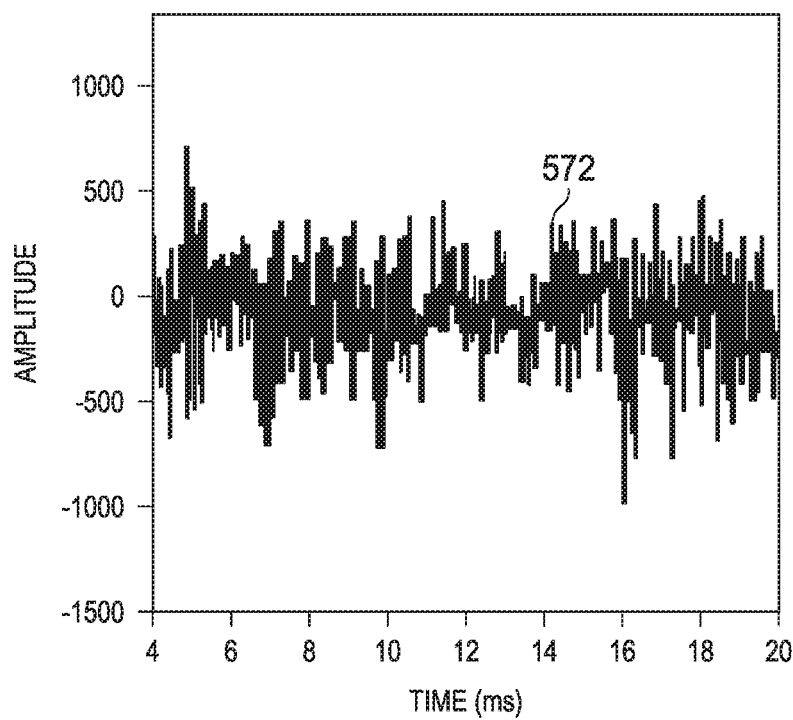

As the clinician moves the mobile device 460 over the surface of the drape 440, the amplitude of the audio signals also vary over time as represented audio signals 570 and 572 in FIGS. 5A and 5B, respectively, which are typical of those present with a typical apparatus 400 operating in a reasonably quiet room. Such audio signals 570 and 572 may also have a frequency spectrum within the dynamic frequency range of the microphone 464 or the frequency range of human hearing (e.g., 20 Hz to 20 kHz) as represented by the frequency responses 670 and 672, respectively, shown in FIGS. 6A and 6B. Referring back to FIGS. 5A and 5B, the first set of audio signals 570 may correspond to a first location on the drape 440 where there are no leaks. The audio signals may be sampled and analyzed, and may have amplitudes as shown in FIG. 5A indicating that no fluid leak is present. The second set of audio signals 572 may correspond to a second location on the drape 440 when the clinician moves the mobile device 460 to the second location, and may have amplitudes as shown in FIG. 5B indicating that a fluid leak is present. As can be seen, the amplitudes of the second set of audio signals 572 increased compared to the amplitudes of the first set of audio signals 570 as the clinician moved the mobile device 460 over the surface of the drape 440 from the first location to the second location where the presence of a fluid leak was identified.

The amplitudes of the second set of audio signals 572 also provide an indication of the severity of the fluid leak as well as its specific location. For example, the clinician may set a threshold value that is a maximum amplitude associated with a maximum leakage to be tolerated as described above, i.e., an audio amplitude threshold. The audio amplitude threshold may be used for comparison to the amplitudes of the actual audio signals being analyzed to provide an indication to the clinician or user that the fluid leak it is sufficiently serious to require correction if the audio amplitude threshold is exceeded. The clinician may also set a threshold value that is the maximum difference in amplitudes between the first location and the second location associated with the maximum leakage to be tolerated, i.e., an audio amplitude differential threshold. The audio amplitude differential threshold may be used for comparison to the difference between the amplitudes of the actual audio signals at two locations to provide an indication to the clinician or user that the fluid leak is sufficiently serious to require correction.

Referring back to FIGS. 6A and 6B, the frequency responses 670 and 672 of the audio signals 570 and 572, respectively, may also indicate the presence of a fluid leak. More specifically, the amplitudes of the audio signals 570 and 572 vary over time and may be filtered and processed to generate the frequency responses 670 and 672. The first frequency response 670 corresponds to the first location on the drape 440 as described above where there are no leaks. The second frequency response 672 corresponds to the second location on the drape 440 when the clinician moves the mobile device 460 to the second location, and may have a magnitude indicating that a fluid leak is present. As can be seen, the magnitude of the second frequency response 672 identifies a prominent group of frequencies between about 5 and 10 kHz where the magnitude increased by approximately 30 dB when comparing the frequency response 672 at the second location to the frequency response 670 at the first location indicating the presence of a fluid leak at the second location.

The magnitude of the second frequency response 672 also provides an indication of the severity of the fluid leak as well as its specific location. For example, the clinician may set a threshold value that is a maximum magnitude associated with a maximum leakage to be tolerated as described above, i.e., an audio strength threshold. The audio strength threshold may be used for comparison to the magnitudes of the frequency responses 670 and 672 to provide an indication to the clinician or user that the fluid leak it is sufficiently serious to require correction if the audio strength threshold is exceeded. The clinician may also set a threshold value that is the maximum difference in magnitudes between the first location and the second location associated with the maximum leakage to be tolerated, i.e., a strength differential threshold. The strength differential threshold may be used for comparison to the difference between the magnitudes of the actual frequency responses at the two locations to provide an indication to the clinician or user that the fluid leak is sufficiently serious to require correction.

Figure 7A:
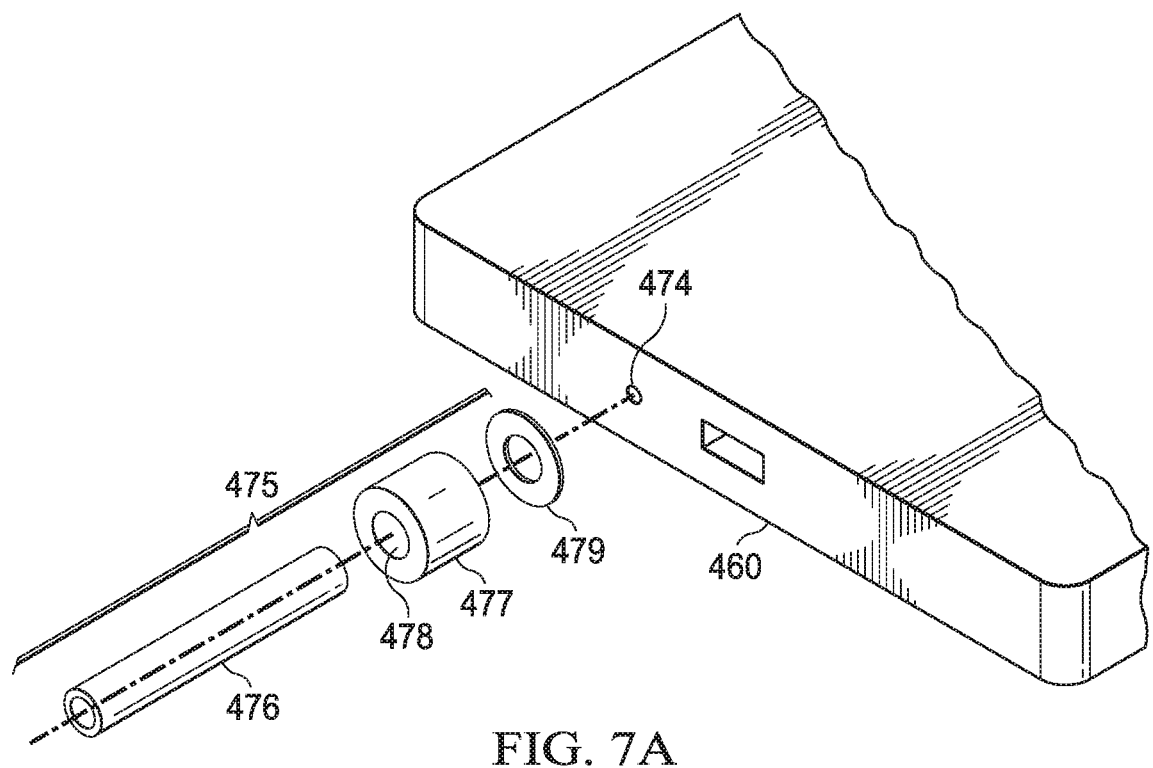
FIGS. 7A and 7B are perspective, schematic views of a microphone resonator assembly that may be used in conjunction with the microphone of a mobile device for detecting sound pressure waves that may be analyzed to detect fluid leaks associated with a drape.
Figure 7B:
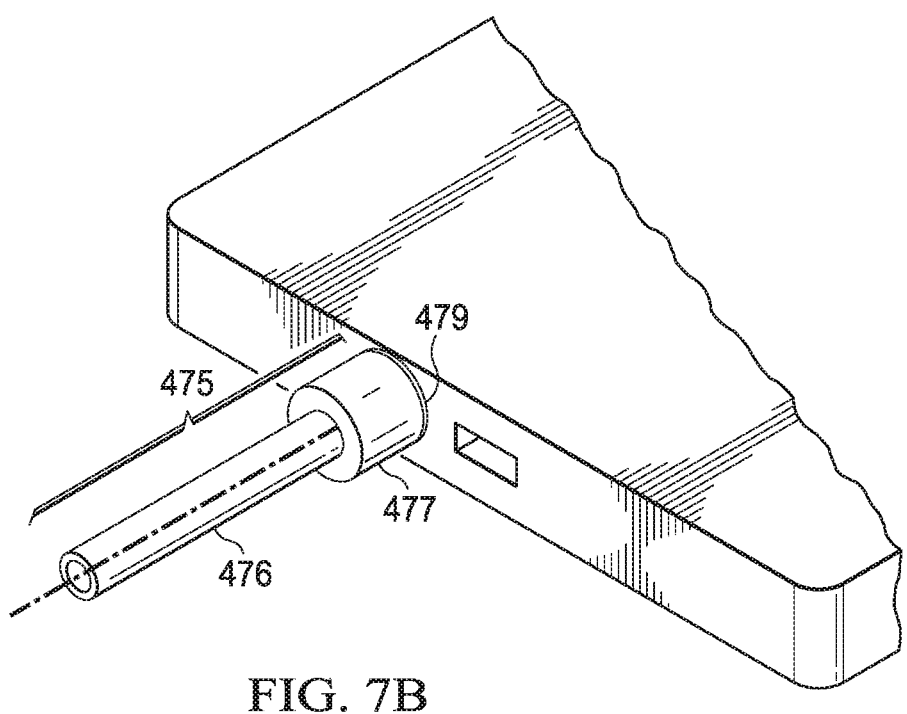

Referring to FIG. 4, the mobile device 460 may include an additional tool fitted with the microphone 464 to facilitate the process of scanning for fluid leaks in the drape 440 or between the drape 440 and the peri-tis sue 442 as described above. Referring more specifically to FIGS. 7A and 7B, the mobile device 460 is shown in a perspective view as including a microphone aperture 474 that extends through the casing of the mobile device 460 through which the microphone 464 receives the sound pressure waves 470. The mobile device 460 may also comprise a microphone resonator 475 shown in an exploded and assembled view that may be fluidly coupled to the microphone 464 through the aperture 474. The aperture 474 may have a diameter in the range of about 2 mm, for example, that may also be smaller than the actual diameter of the microphone 464 embedded within the mobile device 460 adjacent the aperture 474. The microphone resonator 475 comprises a resonator tube 476 that may be mechanically coupled to the mobile device 460 to cover the microphone aperture 474 so that the resonator tube 476 is acoustically coupled to the microphone 464. The microphone resonator 475 may further comprise a cylindrical rubber foot 477 having an aperture 478 extending axially through the cylindrical rubber foot 477 to receive and support the resonator tube 476. The resonator 475 may further comprise an adhesive washer 479 disposed between the cylindrical rubber foot 477 and the casing of the mobile device 460 to support the cylindrical rubber foot 477 and the resonator tube 476 on the casing over the microphone aperture 474.

In one example embodiment of the microphone resonator 475, the resonator tube 476 has a centerline that is aligned with the center of the microphone aperture 474 and the microphone 464 embedded within the mobile device 460. The resonator tube 476 may be constructed from polypropylene or similar material and may be transparent to detect any blockages that might occur in use. The resonator tube 476 may have a length and inside diameter suited to acoustically match a specific frequency range of the sound pressure waves 470 generated by a fluid leak in or around the drape 440 and being sensed by the microphone 464. The frequency range of the sound pressure waves 470 may lie within the frequency range of human hearing (e.g., 20 Hz to 20 kHz) as described above. In one example embodiment, the resonator tube 476 may have an inside diameter in a range between about 2 mm and 6 mm. In another example embodiment, the resonator tube 476 may have an overall length in a range between about 30 mm and 50 mm. In yet another example embodiment, the resonator tube 476 may have an overall length of about 40 mm and an inside diameter of about 4 mm to match the frequency range of human hearing (e.g., 20 Hz to 20 kHz) as described above.

Figure 6A:
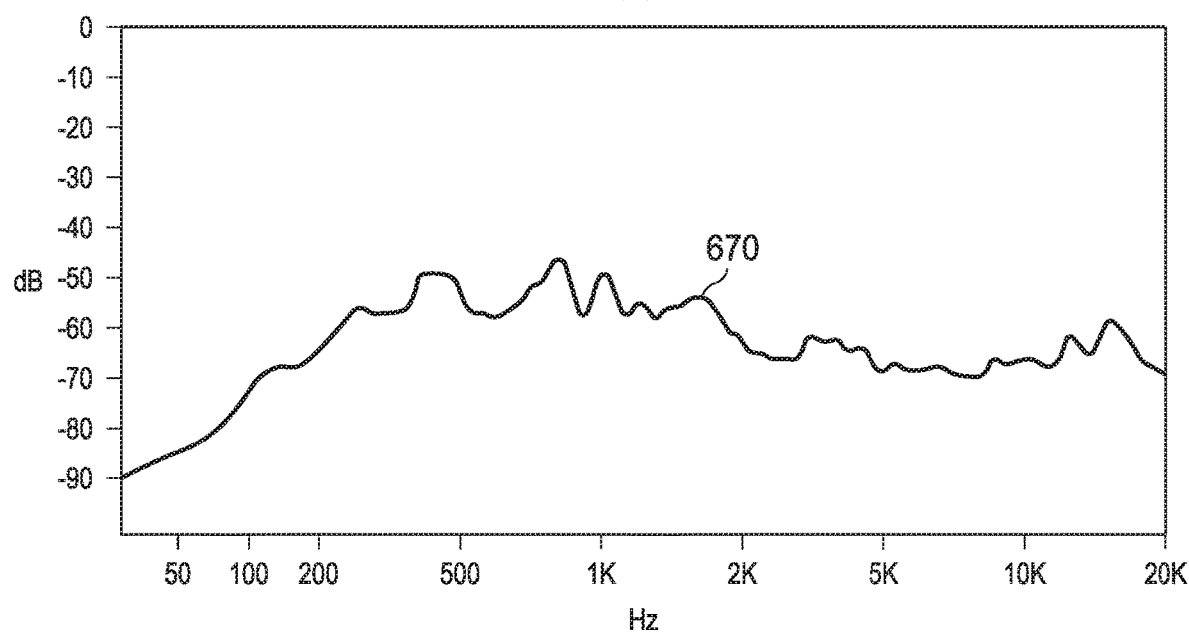
FIGS. 6A and 6B are graphs of frequency response of the audio signals that are examples indicating the detection of fluid leaks associated with the drape, wherein FIG. 6A indicates that no leak is present and FIG. 6B indicates the presence of a fluid leak.
Figure 6B:
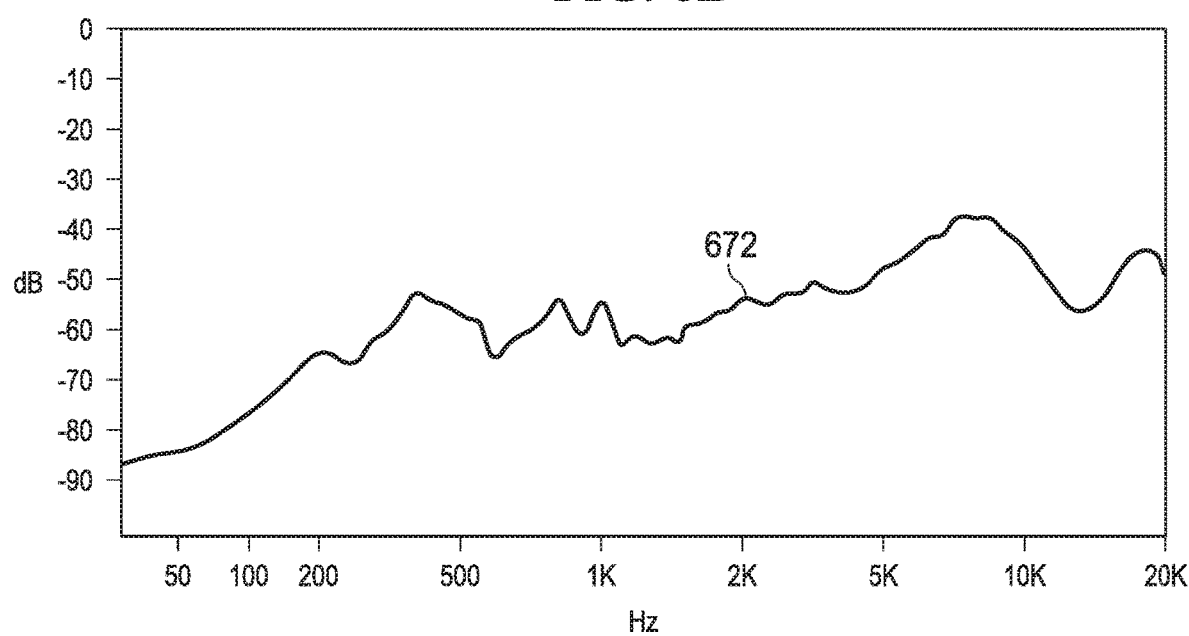

The microphone resonator 475 functions as an attachment to the mobile device 460 to allow the mobile device 460 to reach into tight crevices and creases formed by the drape 440 and functions based on the phenomenon of air resonance within the resonator tube 476, i.e., Helmholtz resonance. In operation, air forced into the resonator tube 476 increases the pressure within the cavity of the resonator tube 476, but when the external force used to push the air into the cavity is removed, the air within the cavity is pushed out again due to the higher pressure. Typically, the air pressure in the cavity decreases as a result of a fluid leak because the negative pressure being applied through the distribution manifold 438 sucks air out of the cavity through the fluid leak associated with the drape 440. When the cavity of the microphone resonator 475 is moved away from the fluid leak, air flows back into the cavity which causes the air pressure in the cavity to return to a normal, ambient pressure. Increasing the audio inlet path from the microphone (i.e., the length of the resonator tube 476) shifts the peaks of the frequency responses 670 and 672 downward in frequency and increases the amplitude, thus aiding and enhancing the ability of the microphone 464 to detect changes in signal energy as shown in FIGS. 6A and 6B as described above. Increasing the inner diameter of the resonator tube 476 may also increase the amplitude of the signal energy, but to a lesser extent.

Figure 8:
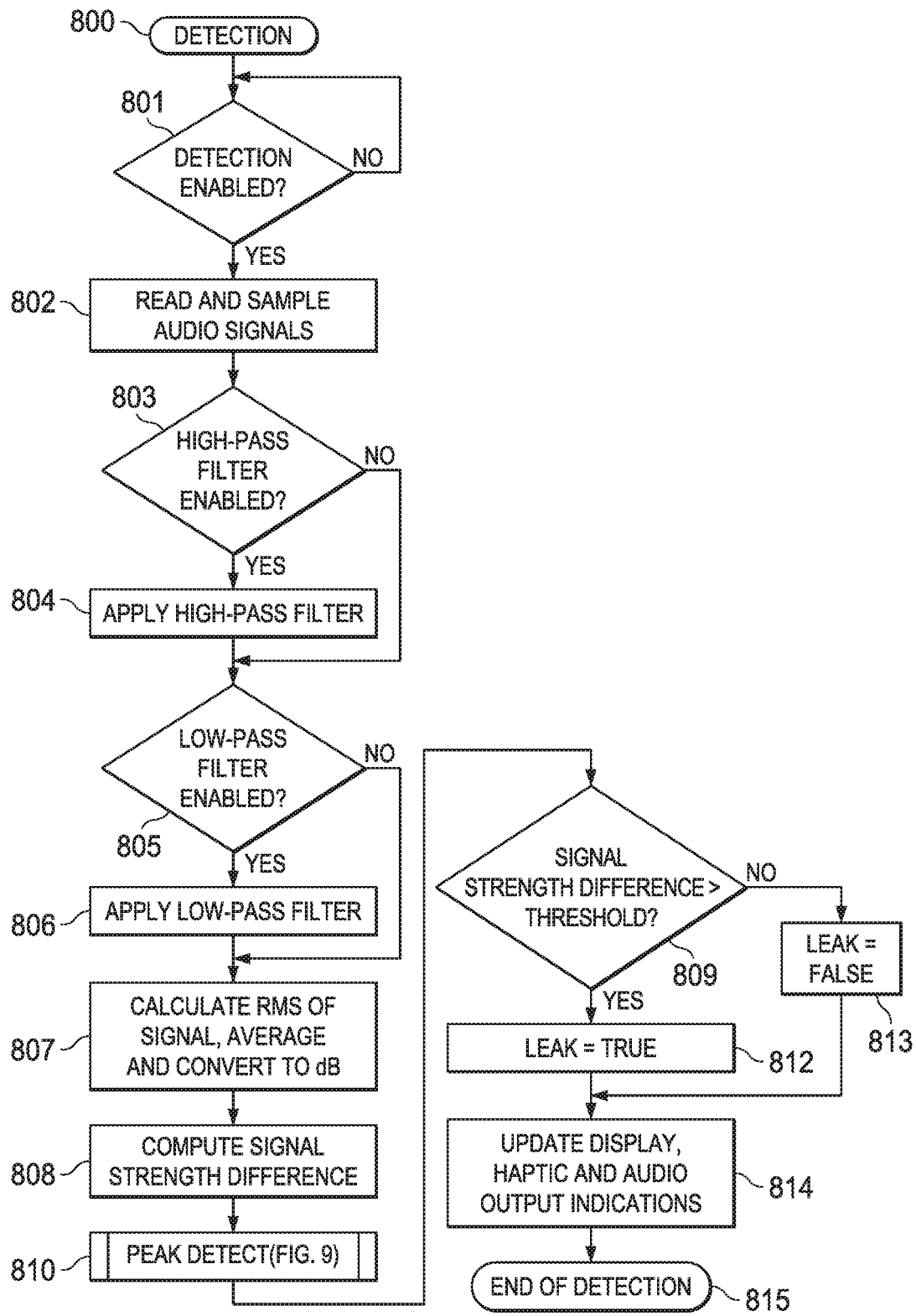
FIG. 8 is a flow diagram of a method for detecting fluid leaks of dressing positioned at a tissue site being treated by a reduced pressure delivery system such as, for example, the system of FIG. 4, including a peak signal detection module for detecting a peak signal for comparison to a detection threshold.

Referring to FIG. 8, a flow diagram or algorithm is shown as one example of a leak detection application that may be a software program implemented on a computer such as, for example, the mobile device 460 as generally described above. The algorithm may embody a method for detecting fluid leaks as shown commencing with the detection of pressure sound waves at 800 using a microphone as described above. The leak detection application determines whether the microphone of a mobile device is enabled to detect pressure sound waves at 801 and, if confirmed, then reads and samples audio signals provided by the microphone at 802. The samples of the audio signals are then processed through an adjustable high-pass filter if enabled at 803 and 804 to remove lower frequency noise that might be caused by human speech, e.g., a cut-off frequency of about 3.5 kHz. The output of the high-pass filter then cascades into an adjustable low-pass filter if enabled at 805 and 806 in order to remove high-frequency components if necessary. The high-pass filter and the low-pass filter comprise a band-pass filter that can be adjusted to remove ambient noise and narrowed to focus on the specific frequency range where the frequency response of the fluid leaks are expected.

The output values from the band-pass filter may then be processed at 807 by calculating the RMS of the signals and then computing the average which may be converted to determine the magnitude or the signal strength (dB) of the pressure sound waves such as, for example, the sound pressure wave 470, representing the "energy" of the sound pressure wave. More specifically, the output values from the band-pass filter may be numerically integrated to approximate the RMS energy over the frequency window and then be further smoothed to provide a rolling-average, e.g., 35 ms slow "impulse" function or a 125 ms fast "exponential" time weighing function as desired. A signal strength value ($SS_2$) of the sound pressure wave may be compared to a previously computed signal strength value ($SS_1$) at 808 by determining the difference between them, i.e., a signal strength difference ($\delta SS$). Successive signal strength differences ($\delta SS$) may be determined in a similar fashion and stored in a database set for subsequent processing to identify fluid leaks proximate a drape.

In one example, the signal strength difference ($\delta SS$) may be compared to a predefined or adjustable signal strength threshold (SST) at 809 such as, for example, the strength deferential threshold described above, to determine whether a fluid leak is present at 812, 813. If the signal strength difference ($\delta SS$) is greater than the signal strength threshold (SST), a fluid leak is not only present, but also may be serious enough to require correction as described above. The leak detection application provides a signal indicating the detection of a fluid leak at 814 on the electronic display of the mobile device (or via other audio and/or haptic outputs as described above). This detection process ends at 815 and is iterative as the microphone of the mobile device is moved slowly across the surface of the drape. Moreover, the fluid detection application may also allow for the signal strength threshold (SST) to be adjusted manually or dynamically to compensate for the changes in the ambient background noise depending on the location of the drape being inspected.

Figure 9:
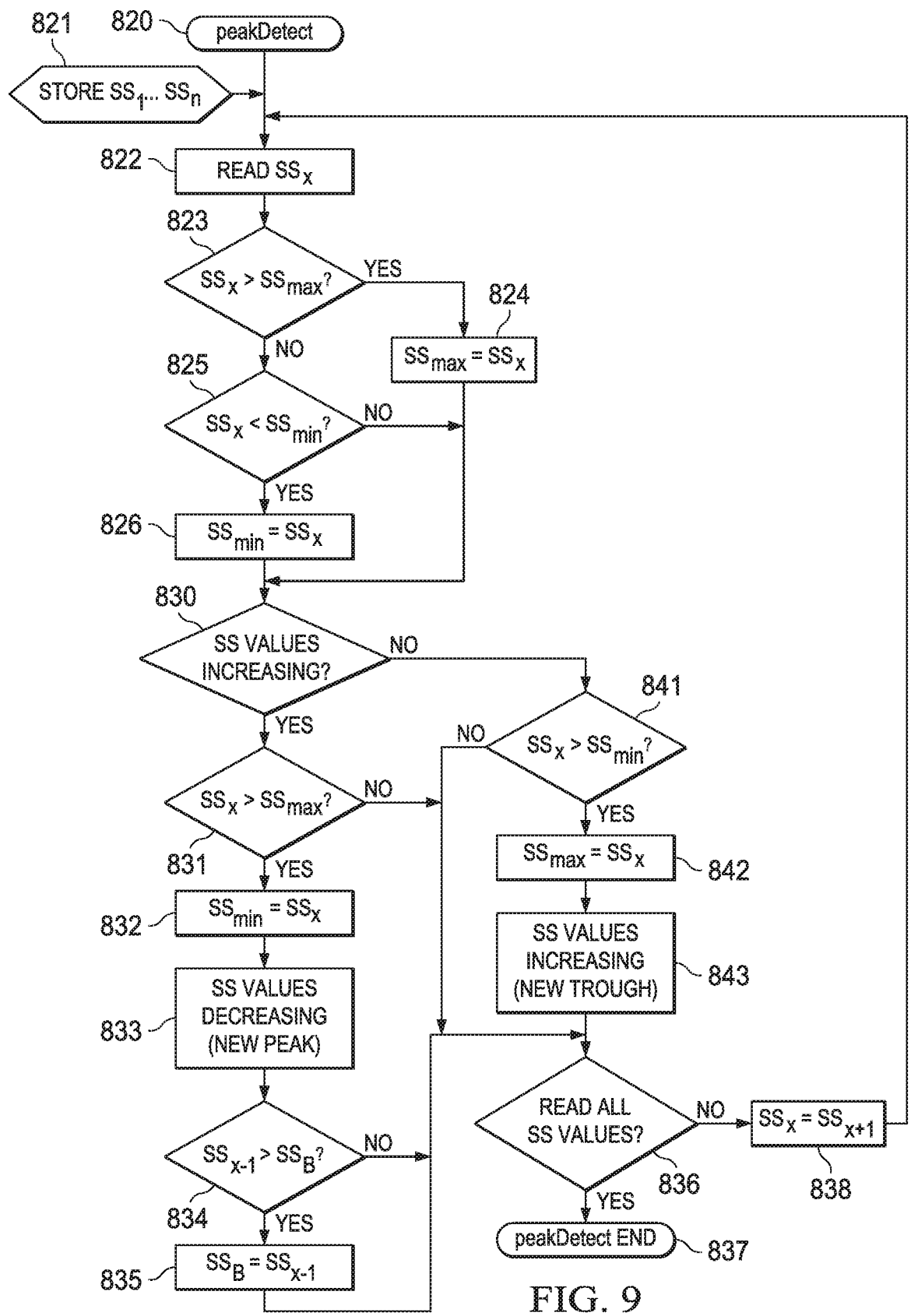
FIG. 9 is a flow diagram of a peak signal detection module for detecting a peak signal for comparison to a detection threshold which may be used in the flow diagram of FIG. 8.

In another example, the leak detection application may also include a peak detection step shown at 810 that stores a block of data representing a sample of signal-strength values (SS) and then reads and processes the samples by comparing successive signal-strength values (SS) in the block of data to determine whether the values in the block of data are increasing toward a peak value indicative of a fluid leak. Referring more specifically to FIG. 9, a flow diagram or algorithm is shown as one example of a peak detection application that may be a software program implemented on a computer such as, for example, the mobile device 460 as generally described above. The peak detection algorithm may embody a method for detecting peaks commencing at 820 with storing a block of data representing a sample of a plurality of signal-strength values (SS) as limited by a set of certain conditions. For example, these conditions may include a maximum and minimum number of data points in the sample that correlates with the speed at which the microphone is being moved over the drape to detect the leaks. The peak detection algorithm then reads successive signal strength values ($SS_1 \ldots SS_n$) in the block of data at 821 to determine whether the current signal strength value ($SS_x$) to be read is greater than the previous signal strength value ($SS_{x-1}$) or signal strength values.

The peak detection algorithm may read the current signal strength value ($SS_x$) at 822 and then determine whether the current signal strength value ($SS_x$) is greater than a maximum signal strength value ($SS_{max}$) at 823 and, if yes, set or reset the maximum signal strength value ($SS_{max}$) to equal the current signal strength value ($SS_x$) at 824. If the current signal strength value ($SS_x$) is not greater than the maximum signal strength value ($SS_{max}$), the peak detection algorithm may then determine whether the current signal strength value ($SS_x$) is less than a minimum signal strength value ($SS_{min}$) at 825 and, if yes, set or reset the minimum signal strength value ($SS_{min}$) to equal current signal strength value ($SS_x$) at 826. Whether or not the maximum and minimum signal strength values are set or reset, the peak detection algorithm then determines whether the successive signal strength values are increasing or decreasing in order to detect signal strength peaks and troughs in the successive signal strength values ($SS_1 \ldots SS_n$) stored in the block of data.

More specifically, the peak detection algorithm in one example determines whether the current signal strength value ($SS_x$) is greater than the previous signal strength value ($SS_{x-1}$) at 830 in order to determine whether the signal strength values (SS) are increasing or decreasing. In another example, the peak detection algorithm may determine whether the current signal strength value ($SS_x$) is greater than a series of previous signal strength values. The peak detection algorithm may next determine which of two paths to take based on whether the historic values appear to be increasing or decreasing in signal strength at 830. The algorithm may initially be set to make an arbitrary determination that the historic values are increasing, but subsequently make such determination based on whether the path previously taken went through 833 or 843. If the algorithm determines that the signal strength values are increasing, the algorithm next determines whether the current signal strength value ($SS_x$) is less than the maximum signal strength value ($SS_{max}$) at 831. If the answer is yes, then the direction of the signal strength value (SS) is decreasing from the previous signal strength value ($SS_{x-1}$) indicating that a peak value has been found. The minimum signal strength value ($SS_{min}$) is set to equal the current signal strength value ($SS_x$) at 832 indicating a new leak at 833 so that the next reduction in the magnitude of the signal strength value (SS) can be tracked.

The peak detection algorithm may then determine whether the previous signal strength value ($SS_{x-1}$), which inferentially is the newly detected peak as described above, is bigger than any previous signal strength value at 834. If yes, the peak detection algorithm sets the previous signal strength value ($SS_{x-1}$) as a biggest signal strength value ($SS_B$) that is used in subsequent comparisons. If the previous signal strength value ($SS_{x-1}$) is not greater than the biggest signal strength value ($SS_B$) at 834 or if the biggest signal strength value ($SS_B$) is reset to the previous signal strength value ($SS_{x-1}$) at 835 or the current signal strength value ($SS_x$) was initially determined not to be less than the maximum signal strength value ($SS_{max}$) at 831, then the peak detection algorithm determines whether all of the signal strength values ($SS_n$) have been read at 836. If not, the peak detection algorithm resets the current signal strength value ($SS_x$) as the next signal strength value ($SS_{x+1}$) at 838 to be processed in a similar fashion commencing at 822. However, if the peak detection algorithm determines that all the signal strength values ($SS_n$) have been read at 836, the peak detection algorithm returns to the leak detection application 800 described above to test the biggest signal strength value ($SS_B$) against the signal strength threshold (SST) at 809.

As indicated above, the peak detection algorithm determines which path to take at 830 depending on whether the path last taken went through 833 (new peak) or 843 (new trough) or no change. If the algorithm determines that the signal strength values are decreasing at 830, the algorithm next determines whether the current signal strength value ($SS_x$) is greater than the minimum signal strength value ($SS_{min}$) at 841. If the answer is yes, then the direction of the signal strength value (SS) is increasing from the previous signal strength value ($SS_{x-1}$) indicating that a trough value has been found. The maximum signal strength value ($SS_{max}$) is set to equal the current signal strength value ($SS_x$) at 842 indicating a new trough at 843 so that the next increase in the magnitude of the signal strength value (SS) can be tracked. If the answer at 841 is no or the maximum signal strength value ($SS_{max}$) is set to equal the current signal strength value ($SS_x$) at 843, then the peak detection algorithm proceeds to determine whether all the signal strength values ($SS_n$) have been read and processed as described above.

Figure 10:
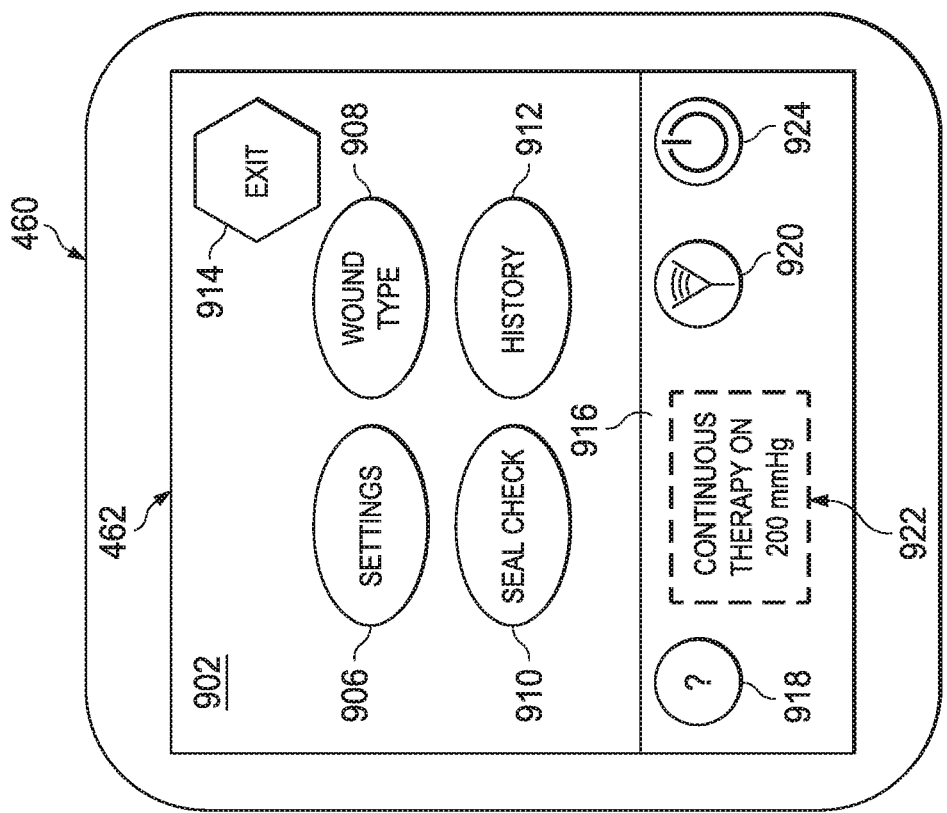
FIG. 10 is a screen shot of an exemplary graphical user interface of a reduced pressure delivery system showing an embodiment for enabling a clinician to select a "seal check" function to locate fluid leaks that exist at the drape.

The electronic display device 462 may be programmed to display a graphical user interface (GUI) displaying information related to the analysis and processing of the audio signals for detecting fluid leaks including identifying their location and severity. Referring now to FIG. 10, a screen shot of a first GUI 902 may include a number of selectable graphical elements, including a "settings" soft-button 906, "wound type" soft-button 908, "seal check" soft-button 910, and "history" soft-button 912. A clinician or other user may select any of these functions (i.e., settings, wound type, seal check, or history), to cause the mobile device 460 to present the user with another GUI for performing the selected function. In addition, an "exit" soft-button 914 may be available to the user to exit the current GUI 902. The seal check soft-button 910 may be programmed to access the leak detection application which operates as described above. It should be understood that the GUI 902 is exemplary and that other and/or alternative functions and selection elements may be provided by the electronic display device 462 on the mobile device 460 to the user.

An information region 916 on the GUI 902 may include selectable graphical elements and display other information in which the user may be interested. For example, a "help" soft-button 918 may be displayed to enable the user to receive help about the delivery system 402 or particular functions currently being displayed on the GUI 902. An "on-off" soft-button 920 may enable a user to selectively turn the delivery system 402 on and off, and status information 922 may notify the user of current status of the delivery system 402. For example, the status information 922 may indicate that the delivery system 402 is (i) operating in a continuous therapy mode, (ii) is on, and (iii) is operating to provide a reduced pressure of 200 mmHg A "lock" soft-button 924 may enable the user to lock the GUI 902 to prevent an inadvertent contact with the GUI 902 to cause the delivery system 402 to respond.

Figure 11:
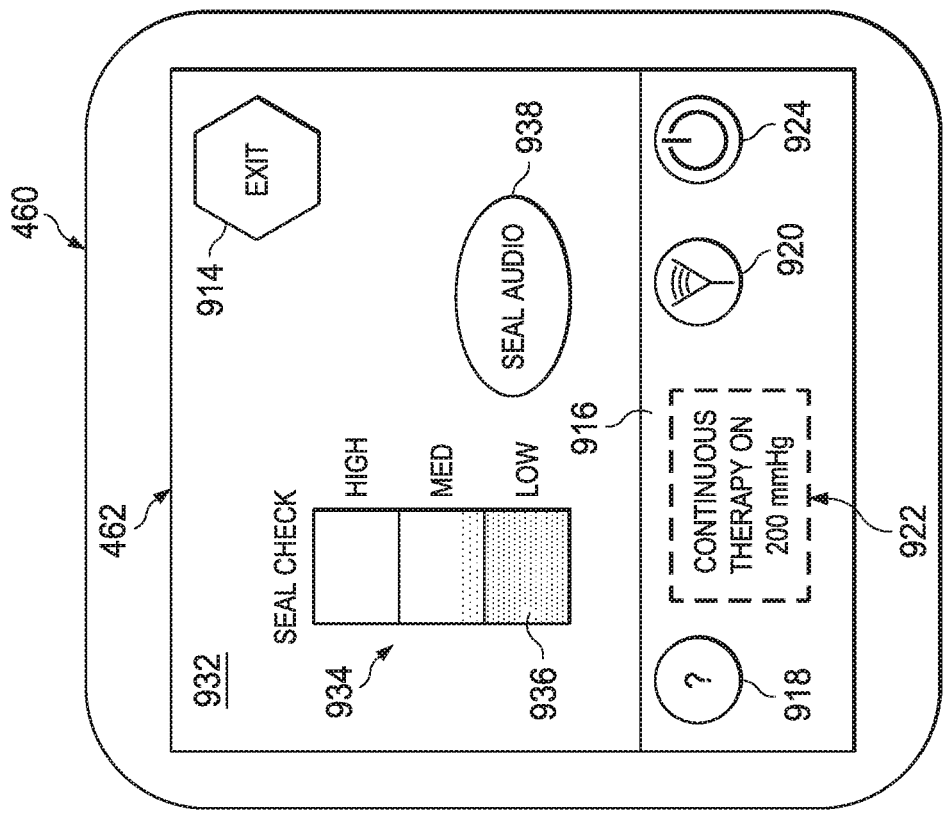
FIG. 11 is a screen shot of another exemplary graphical user interface of a reduced pressure delivery system showing an embodiment for enabling a clinician to select a mode for the reduced pressure delivery system to determine whether any fluid leaks exist at the drape.

Referring to FIG. 11, the mobile device 460 may display a second GUI 932 on the electronic display device 462 in response to a user selecting the "seal check" soft-button 910 on the GUI 902 of FIG. 10. The GUI 932 may display a graphical indicator 934 indicative of the pressure and/or severity of a fluid leak. The graphical indicator 934 may be a bar indicator having three levels, including low, medium, and high thresholds for indicating the signal strength difference ($\delta SS$). The graphical indicator 934 may show a dynamic portion 936 that increases and decreases based on the signal strength difference ($\delta SS$) as determined by moving the mobile device 460 from one location to another over the drape 440 as described above. The height of the dynamic region 936 may indicate, for example, the amount of a fluid leak currently being sensed at a tissue site. Although the graphical indicator 934 may be helpful to a clinician for determining the location of a fluid leak, e.g., a fluid leak associated with the drape 440 covering the tissue site 404 and the distribution manifold 438, the graphical indicator 934 may be difficult to view if the electronic display device 462 were a component of the reduced pressure therapy system 401 located several feet away from the drape where the clinician is attempting to locate a fluid leak as opposed to being displayed on the mobile device 460.

So that the clinician may more easily locate the fluid leak at the drape, the mobile device 460 may generate an audible sound or other graphical or haptic output indicative of the location of a fluid leak sensed by the microphone 464 of the mobile device in conjunction with the level of a particular signal strength difference ($\delta SS$) sensed by the mobile device 460. The clinician may select a "seal audio" soft-button 938 to toggle or mute and unmute an audible fluid leak location sound off and on (i.e., mute and unmute). The audible fluid leak location sound may be altered in response to the changes of the magnitude of the signal strength difference ($\delta SS$). For example, if pressure at the tissue site increases in response to moving the mobile device 460 from one location to another on the drape, the audible fluid leak location sound may be altered to indicate to the clinician that the fluid leak has been located.

The audible fluid leak location sound may change in frequency, volume, or pitch. Alternatively, a "Geiger counter" sound may be produced during the seal check, where a tone speed increases or decreases depending upon the severity of the fluid leak. For example, if the clinician is "cold" with respect to the location of the fluid leak, the Geiger counter sound may beep slowly. When the clinician approaches near the fluid leak of the drape, then the Geiger counter sound may increase as the mobile device gets closer to the fluid leak. In another embodiment, the audible fluid leak location sound may be a recorded message, such as "cold," "warmer," and "hot." In another example, a "water dripping" sound may be generated to represent that a fluid leak (e.g., air leak) exists. It should be understood that nearly any sound may be utilized to indicate the presence and/or severity of a fluid leak to help the clinician locate the fluid leak and assess the severity to determine whether corrective measures are necessary. Because the microphone of a mobile device and even a human ear are more sensitive than human eyes, the use of an audible sound to indicate the presence and/or severity of a fluid leak may enable the clinician to more easily correct the fluid leak at the drape than a graphical indicator.

Regarding FIG. 11A, a bar indicator 940a may display a dynamic region 942a indicative of a level of the signal strength difference ($\delta SS$). The dynamic region 942a is shown to be within a "low" fluid leakage level and have a corresponding pattern (e.g., lightly shaded) or color (e.g., green). A threshold level indicia 944 may be representative of a signal strength threshold (SST) level that may be preset by a clinician or manufacturer of the mobile device 460, where an alarm or other response may be generated in response to the fluid leakage parameter crossing the signal strength threshold (SST) level. Referring to the bar indicator 940b in FIG. 11B, the dynamic region 942b increases above the threshold level indicia 944, thereby causing an alarm to be generated and the delivery system 402 to enable a clinician to identify the location of the fluid leak and assess the relative severity of the fluid leak. The dynamic region 942b may be changed in pattern (e.g., medium shade) or color (e.g., yellow) to represent that the fluid parameter is currently in the medium range. If, for example, the fluid parameter increases to cause the dynamic region 942 to enter into a high range, then the dynamic region 942 may be changed in pattern (e.g., solid color) or color (e.g., red). Other graphical features may be used, such as flashing or otherwise, to provide the clinician with visual information to make it easier to determine the urgency for corrective measures for sealing the leak.

Referring to FIG. 11C, a time sequence 946a is shown to include a number of graphic bars 948a-948n over a time period between time $T_0$ and $T_n$. Graphic bars 948a-948n indicate that the signal strength difference ($\delta SS$) is at a low fluid leakage level as the mobile device is moved over the drape from one location to another. However, as shown in FIG. 11D, graphic bar 948n+4 at time $T_{n+4}$ increases above the signal strength threshold (SST) as represented by the threshold level indicia level 950. Referring to FIGS. 11E and 11F, a signal strength difference ($\delta SS$) level is shown alphanumerically in display fields 952a and 952b, respectively. As shown, the fluid leakage rate is at "1" which represents a low level leakage, and "5" which represents a higher level leakage. In one embodiment, ranges between 0-3 may represent a low level leakage, 4-6 may represent a medium level leakage, and 7-10 may represent a high level leakage. Each level of leakage may represent a corresponding flow rate and the digits may change color (e.g., green, orange, and red) depending on the fluid leakage level. In an alternative embodiment, letters, such as "A"-"F," may be displayed.

Referring to FIGS. 11G and 11H, pie charts 954a and 954b, respectively, may be displayed that show leakage levels 956a and 956b, respectively, that indicate fluid leakage during operation of a tissue treatment system. One or more threshold levels 958 may be shown and used to identify when a fluid leakage exceeds the threshold, thereby causing a fluid leakage alarm to be initiated. If multiple threshold levels are used, each may represent a different leakage level (e.g., low, medium, or high) and may cause a different alarm, audible and/or visual, to be initiated. Depending on the level of the fluid leakage rate, the color or pattern may change. In addition, an audible sound may be altered in response to the fluid leakage rate increasing or decreasing above or below a threshold level.

Figure 12A:
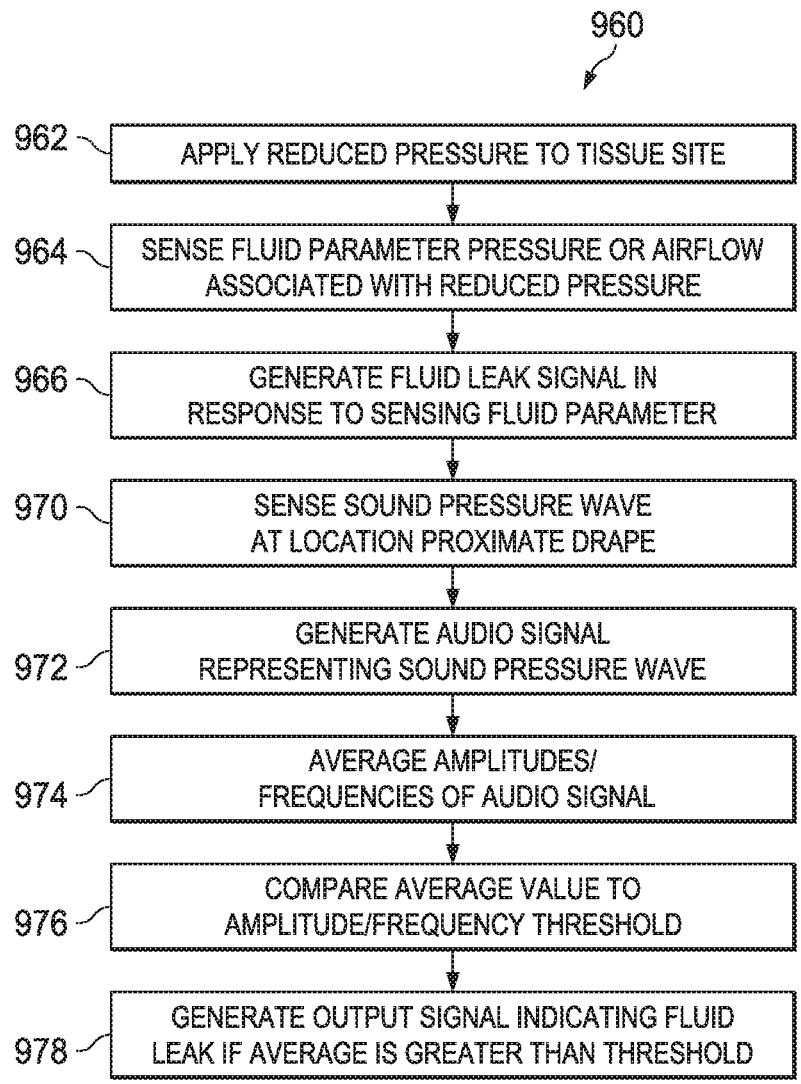
FIGS. 12A and 12B are flow charts of an exemplary process for generating an output signal indicating the presence of a fluid leak at a specific location when the amplitude or frequency information of an audio signal is greater than a threshold value at that location, or greater than the amplitude or frequency information at another location, respectively.

Referring to FIG. 12A, a process 960 for determining location of a fluid leak is provided. The process 960 starts at step 962, where a reduced pressure may be applied to a tissue site. At step 964, a fluid parameter associated with the reduced pressure may be sensed. The fluid parameter may include a fluid flow rate, fluid pressure, or otherwise. In one embodiment, the fluid parameter is sensed at the tissue site. In another embodiment, the fluid parameter is sensed in a reduced pressure conduit of the delivery system. It should be understood that the fluid parameter may be sensed by any type of sensor that is sensitive enough to sense changes in the fluid parameter that are meaningful to a clinician when attempting to locate and seal a fluid leak. For example, a fluid flow transducer may be configured to sense changes in fluid flow rate between approximately 0.1 liters per minute and 2.0 liters per minute and have a resolution of approximately 0.01 liters per minute.

At step 966, a fluid leak signal may be generated in response to sensing the fluid parameter. The fluid leak signal may be one of a variety of different visual graphics or audible sounds. For example, continuous tones with varying frequency, pitch or volume, for example, may be utilized. Alternatively, discrete tones with varying length or frequency may be utilized. Still yet, recorded messages, sounds, or otherwise may be utilized. It should be understood that any sound or combination of sounds may be utilized as an audible fluid leak location sound. At step 970, a sound pressure wave propagating from the drape of a dressing may be sensed at a first location proximate the drape. At step 972, a first audio signal may be generated representing the sound pressure wave. At step 974, an amplitude average of the amplitudes of the first audio signal may be computed. At step 976, the amplitude average of the first audio signal may be compared to an amplitude threshold indicative of a fluid leak at the first location. And then at step 978, an output signal indicating the presence of a fluid leak at the first location may be generated if the amplitude average is greater than the amplitude threshold.

Alternatively, the frequencies of the first audio signal may be filtered to pass those frequencies, i.e. filtered frequencies, corresponding to the sound pressure waves at locations proximate the drape. A frequency average of the filtered frequencies of the first audio signal may be computed and compared to a frequency threshold indicative of a fluid leak at the first location so that an output signal indicating the presence of a fluid leak at the first location may be generated if the frequency average is greater than the frequency threshold.

Figure 12B:
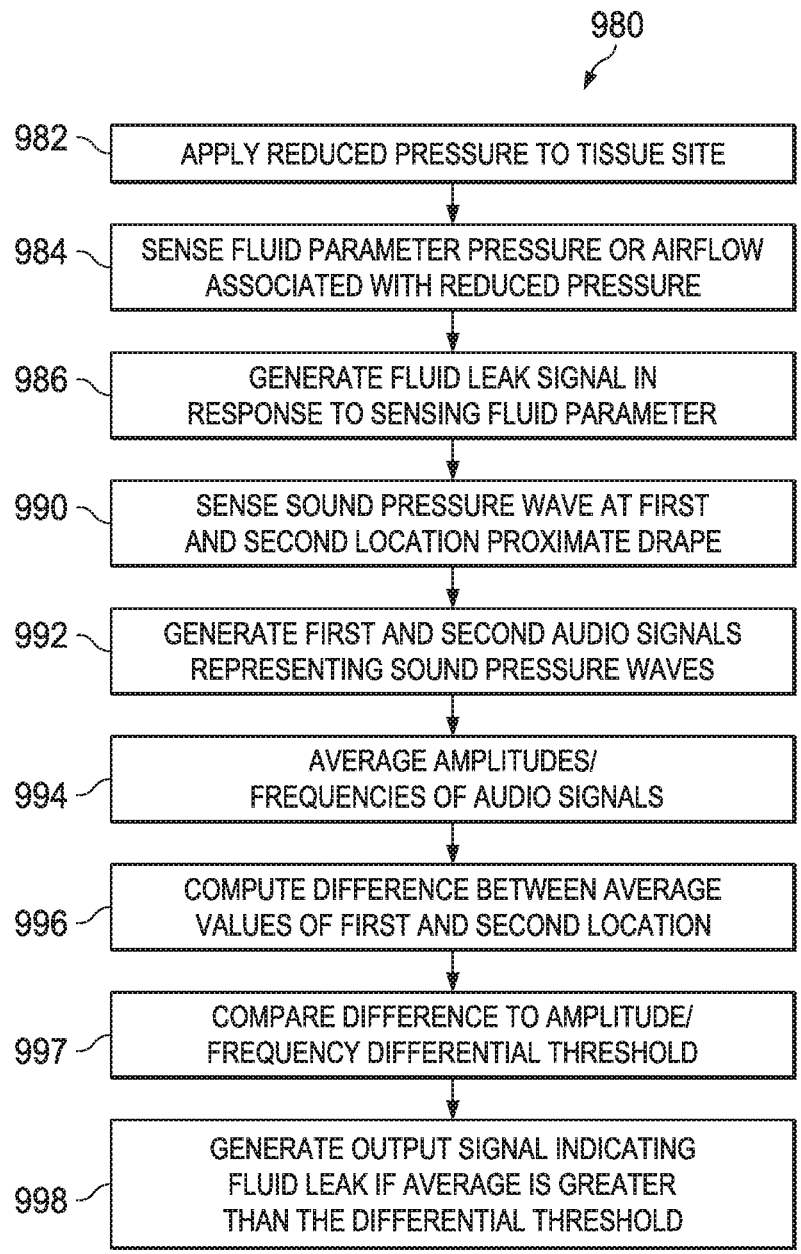

Referring to FIG. 12B, another process 980 for determining location of a fluid leak is provided. The process 980 starts at step 982, where a reduced pressure may be applied to a tissue site. At step 984, a fluid parameter associated with the reduced pressure may be sensed. The fluid parameter may include a fluid flow rate, fluid pressure, or otherwise. It should be understood that the steps are substantially similar to steps 960, 962 and 964 described above. At step 986, a fluid leak signal may be generated in response to sensing the fluid parameter. The fluid leak signal may be one of a variety of different visual graphics or audible sounds as described above with respect to step 966. At step 990, a sound pressure wave propagating from the drape of a dressing may be sensed at a first location and the second location proximate the drape. At step 992, a first audio signal and a second audio signal may be generated representing the sound pressure waves. At step 994, an amplitude average of the amplitudes of the first audio signal and the second audio signal may be computed. At step 996, a difference between the average values of the first location and the second location may be computed, and then the difference may be compared to an amplitude differential threshold at step 997. And then at step 998, an output signal indicating the presence of a fluid leak may be generated if the amplitude average is greater than the amplitude differential threshold.

Alternatively, the frequencies of the first audio signal and the second audio signal may be filtered to pass those frequencies, i.e. filtered frequencies, corresponding to the sound pressure waves at locations proximate the drape. A frequency average of the filtered frequencies of the first audio signal and the second audio signal may be computed and compared to a frequency differential threshold indicative of a fluid leak so that an output signal indicating the presence of a fluid leak may be generated if the frequency average is greater than the frequency threshold at the second location.

Figure 13:
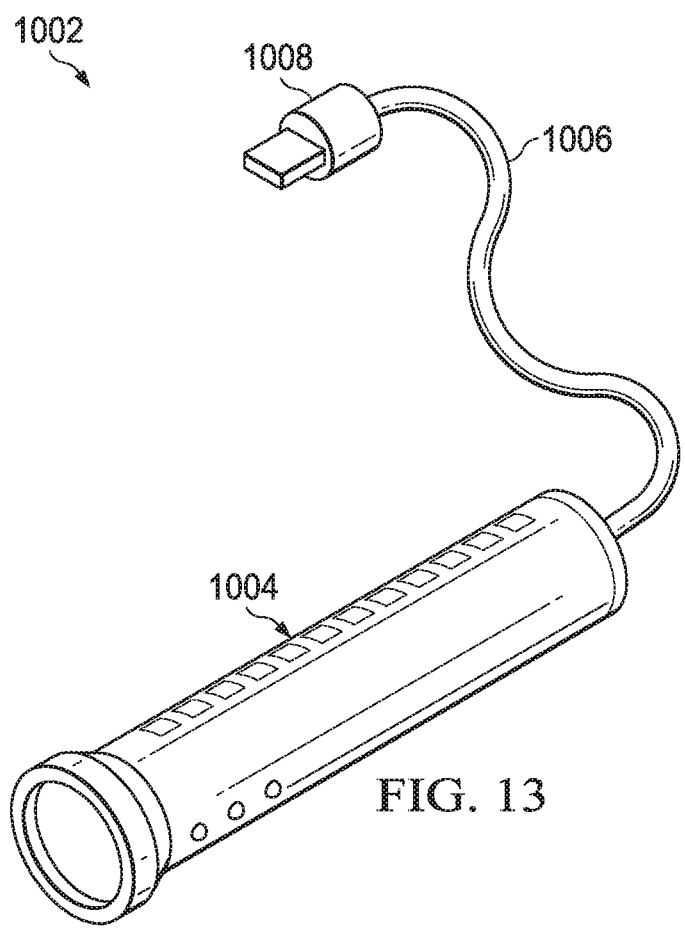
FIG. 13 is a perspective, schematic view of an exemplary leak detection assembly, including a leak detection tool, that may be used for detecting sound pressure waves that may be analyzed to detect fluid leaks associated with a drape.

The principles of the present disclosure may also be applied to embodiments which do not require the use of a mobile device, such as mobile device 460. For example, in place of a mobile device, a separate hand-held portable device may be employed, which may be compatible and used with existing negative-pressure therapy systems, such as the V.A.C.® systems, commercially available from Kinetic Concepts Inc., of San Antonio, Tex. USA. Thus, referring now to FIG. 13, an example, illustrative embodiment of a leak detection assembly 1002 is shown. In this example embodiment, the leak detection assembly 1002 may include a leak detection tool 1004 and a cable 1006. The cable 1006 may be connected at one end to the leak detection tool 1004 and at the other end to a reduced pressure therapy system, and may allow for electrical communication between the leak detection tool 1004 and the reduced pressure therapy system. The cable 1006 may include a connector 1008, which may be for operatively connecting the cable 1006 to a connection port on a delivery system, such as delivery system 402. For example, the connector 1008 may be a USB connector for connection to a USB port. In such example embodiments, the software described above with respect to other example embodiments may be operative for controlling functions of the leak detection tool 1004. For example, the software may be resident on the delivery system 402, and more specifically in the controller 406.

FIG. 14 collectively provides multiple views of an alternative example embodiment of a hand-held version of the leak detection tool 1004. Referring first primarily to FIG. 14A, the leak detection tool 1004 may include a body 1006, which may be in the form of a wand-like housing for components of the leak detection tool 1004. For example, the body 1006 of the leak detection tool 1004 may include a handle portion 1008, a guidance region 1010, a sound energy collector 1012, and a display 1014. In some embodiments, the guidance region 1010 may include one or more contours for allowing a user to obtain a more controlled grip with a thumb or other finger. Referring now also to FIG. 14B, the leak detection tool 1004 may further include a port 1016, which may allow connection to a cable, such as cable 1006 of FIG. 13, which may be used to electrically couple the leak detection tool 1004 to the delivery system 402 of the reduced pressure therapy system 401. For example, the port 1016 may be a USB port, mini-USB port, micro-USB port, or any other type of suitable port. Alternatively or additionally, the port 1016 may include a wireless transceiver, for wirelessly communicating with such-enabled delivery systems. For example, the port 1016 may include a transceiver capable of communications via Bluetooth®, ZigBee®, WI-FI, cellular, or other signal protocol. Additionally, embodiments of the leak detection tool 1004 which may communicate wirelessly with a therapy unit may further include a battery to allow for cordless operation of the leak detection tool 1004. In addition to increased convenience for a user, cordless operation may also allow use with present or future therapy systems that may not include USB or other wired connection ports.

Figure 14A:
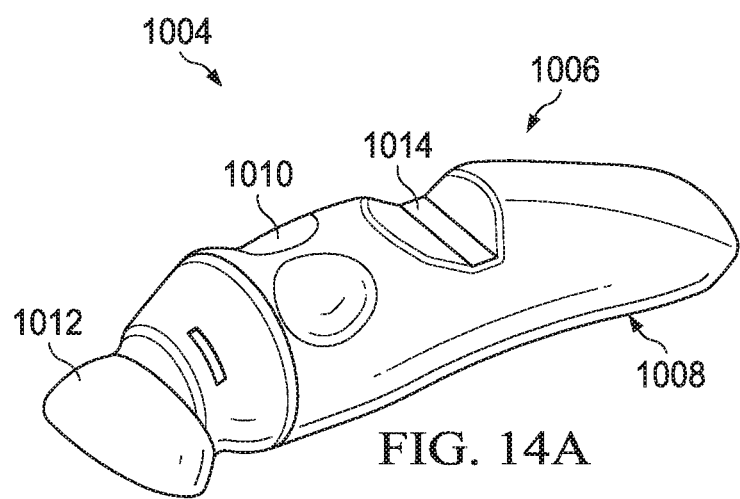
FIGS. 14A-14D are perspective, schematic views of another exemplary leak detection tool, that may be used for detecting sound pressure waves that may be analyzed to detect fluid leaks associated with a drape.
Figure 14B:
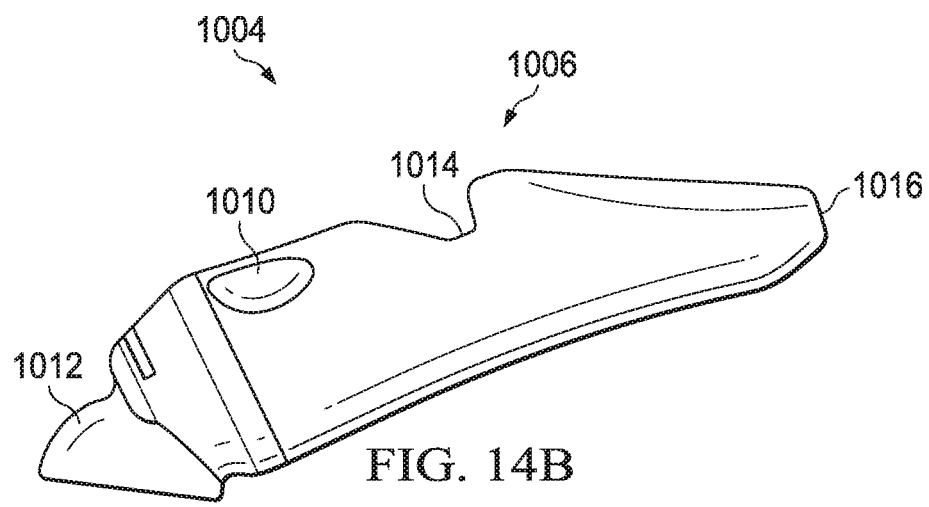
Figure 14C:
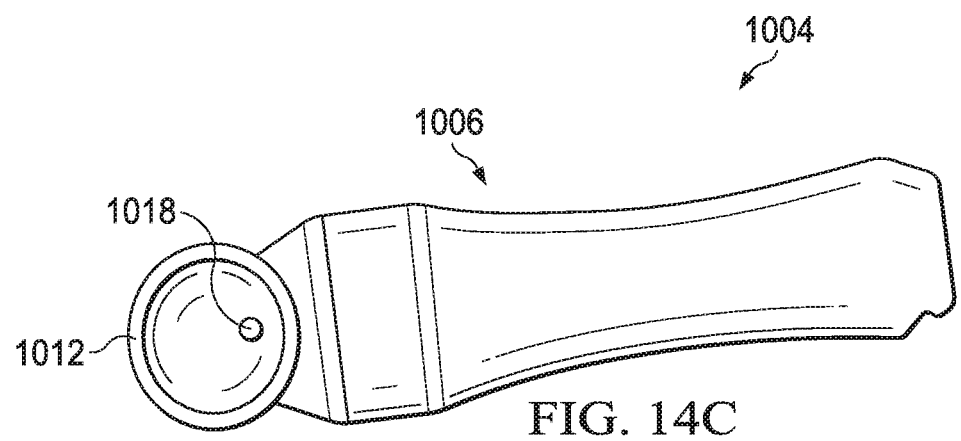
Figure 14D:
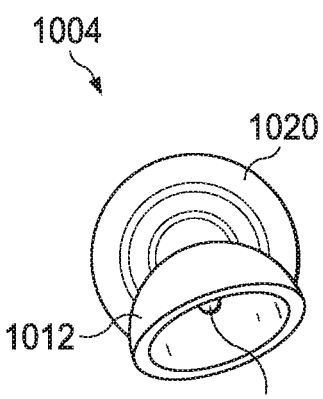

Referring now primarily to FIGS. 14C-14D, a bottom, or underside, view of the leak detection tool 1004 is shown. In FIG. 14C, the underside or inside cavity of the sound energy collector 1012 including a portion of a microphone 1018 may be seen. In addition to the possible types and configurations of microphones previously discussed with respect to other embodiments, the microphone 1018 may be an ultrasonic microphone. Additionally, as shown in FIG. 14D, the sound energy collector 1012 may be attached to a swivel base 1020, which may be part of the body 1006 of the leak detection tool 1004. The swivel base 1020 may allow for the sound energy collector 1012 to pivot as it comes into contact with a surface, to provide good reception of sound energy that may propagate from the surface, such as a wound drape, while also providing ease of use.

Referring again to FIG. 14A, the display 1014 of the body 1006 of the leak detection tool 1004 may include one or more indicators, such as lights, for alerting a user when the leak detection tool 1004 has identified a possible area of a test surface, such as a wound drape, where a leak may be present. For example, in some embodiments, the display 1014 may include one or more LEDs, which may be part of a filtering and detection circuitry positioned within the body 1006 of the leak detection tool 1004. The LEDs may illuminate and display different colors depending on the input detected from the test surface. In one illustrative embodiment, an LED of the display 1014 may emit a green light if no leak conditions are detected, a yellow light if a potential leak is detected, and a red light if a likely leak source has been identified. As previously discussed to some extent, the software for operation of the leak detection tool 1004 may be either stored on a controller, such as controller 406, of the delivery system 402, or on a circuitry associated with a processor of the leak detection tool 1004.

The previous description is of preferred embodiments for implementing the invention, and the scope of the invention should not necessarily be limited by this description. The scope of the present invention is instead defined by the following claims.

We claim:

1. A system for performing reduced pressure tissue therapy, comprising:
   a reduced pressure delivery system configured to apply a reduced pressure provided by a reduced pressure source to a tissue site;
   a drape configured for positioning over the tissue site to maintain reduced pressure at the tissue site;
   a microphone operable to be positioned at a first location proximate the drape to sense a sound pressure wave propagating from the drape at the first location, and configured to generate a first audio signal having amplitude and frequency components; and
   a computing device coupled to the microphone and configured to:
      filter frequency components of the first audio signal,
      compare a frequency average of the filtered frequencies to a frequency threshold indicative of a fluid leak at the first location, and
      generate an output signal indicating a presence of a fluid leak at the first location if the frequency average is greater than the frequency threshold.

2. The system according to claim 1, wherein the computing device is a mobile device.

3. The system according to claim 2, wherein the mobile device includes the microphone.

4. The system according to claim 1, wherein the computing device is further configured to provide an indication that a leak exists at the first location based on the location of the microphone relative to the first location.

5. The system according to claim 1, wherein the microphone is operable to be positioned at a second location proximate the drape to sense a sound pressure wave propagating from the drape at the second location, and configured to generate a second audio signal having amplitude and frequency components, and wherein the computing device is further configured to receive and process the second audio signal to determine a presence of a fluid leak at the second location.

6. The system according to claim 1, wherein the computing device is further configured to commence processing the first audio signal after reduced pressure is increased to a predetermined target pressure.

7. The system according to claim 1, wherein the computing device is further configured to inhibit processing the first audio signal when reduced pressure is being applied to maintain reduced pressure at the tissue site proximate a predetermined target pressure.

8. The system according to claim 5, wherein the computing device is configured to filter frequency components of the first audio signal and the second audio signal to pass filtered frequencies corresponding to the sound pressure waves at locations proximate the drape, and further configured to compute a first frequency average of the filtered frequencies of the first audio signal and a second frequency average of the filtered frequencies of the second audio signal, and to compute a frequency differential between the second frequency average and the first frequency average, and further configured to generate an output signal indicating the presence of a fluid leak if the frequency differential is greater than a frequency differential threshold indicative of a fluid leak at the second location.

9. The system according to claim 8, wherein the frequency averages are converted to a signal strength value of the sound pressure waves.

10. The system according to claim 1, wherein the computing device further comprises an electronic display to provide information relating to changes in the sound pressure wave indicative of a severity of the fluid leak.

11. The system according to claim 1, wherein the computing device further comprises an audio output to provide information relating to changes in a magnitude of the first audio signal indicative of a severity of the fluid leak.

12. The system according to claim 1, wherein the computing device further comprises a resonator tube acoustically coupled to the microphone and having a length and an inside diameter acoustically matching a frequency range associated with the sound pressure waves sensed by the microphone.

13. The system according to claim 1, wherein the computing device further comprises an electronic display configured to display a graphical user interface that includes a selectable element to cause the computing device to enter into a leak location mode.

14. The system according to claim 13, wherein the computing device is further configured to generate a graphical indicator indicative of the amplitude components of the first audio signal and changes in the amplitude components the first audio signal while in the leak location mode.

15. The system according to claim 13, wherein the computing device is further configured to generate a graphical indicator indicative of the frequency components of the first audio signal and changes in the frequency components the first audio signal while in the leak location mode.

16. The system according to claim 15, wherein the computing device is further configured to generate a graphical indicator indicative of the frequency components of the first audio signal as filtered and averaged while in the leak location mode.

17. The system according to claim 1, further comprising:
a conduit fluidly connected between the reduced pressure delivery system and the tissue site, and configured to apply the reduced pressure provided by the reduced pressure delivery system to the tissue site;
a fluid sensor in a fluid communication with the conduit and in electrical communication with a processing unit of the reduced pressure delivery system, and configured to sense a fluid parameter within the system and generate a fluid sensor signal in response to a change in the fluid parameter within the system; and
an output device in communication with the processing unit, wherein the processing unit is configured to communicate a fluid leak signal to the output device to generate an alarm signal when the value of the fluid parameter indicates a possible fluid leak.

18. The system according to claim 17, wherein the processing unit is further configured to determine that the fluid sensor signal crosses a threshold value, to generate an alarm signal in response to determining that the fluid sensor signal crossed the threshold value;
and to communicate the alarm signal to the output device to generate an audible alarm signal.

19. The system according to claim 17, wherein the fluid sensor is an airflow sensor.

20. The system according to claim 17, wherein the fluid sensor is a pressure sensor.

21. An apparatus for detecting fluid leaks in a reduced pressure therapy system, comprising:
a housing sized and adapted to be in the form of a hand-held tool;
a microphone positioned within the housing and operable to sense a sound pressure wave propagating from a drape positioned over a tissue site, and configured to generate a first audio signal;
a computing device electrically coupled to the microphone;
a display disposed on a surface of the housing and configured to provide output indicative of an existence of a fluid leak; and
a communications interface configured to transmit and receive data related to the existence of a fluid leak with a reduced pressure therapy system;
wherein the computing device is configured to:
filter frequency components of the first audio signal,
compare a frequency average of the filtered frequencies to a frequency threshold indicative of a fluid leak at a location, and
generate an output signal indicating a presence of a fluid leak at the location if the frequency average is greater than the frequency threshold.

22. The apparatus of claim 21, wherein the communications interface comprises a wireless transceiver.

23. The apparatus of claim 21, wherein the communications interface comprises a port adapted to receive an electrical communications cable.

24. The apparatus of claim 21, wherein the microphone comprises an ultrasonic microphone.

25. The apparatus of claim 21, wherein the display further comprises at least one LED in electrical communication with a circuitry of the computing device.

26. The apparatus of claim 25, wherein the at least one LED is configured to alternately illuminate green, yellow, and red based on an electrical signal from the circuitry of the computing device, to provide a leak status indication.

27. The apparatus of claim 21, further comprising a sound energy collector affixed to the housing and sized and adapted to capture and direct sound energy to the microphone.

28. The apparatus of claim 21, wherein the microphone comprises an acoustic-to-electric transducer that converts sound to the first audio signal.

* * * * *